(12) United States Patent
Oh

(10) Patent No.: US 10,646,190 B2
(45) Date of Patent: May 12, 2020

(54) RADIOGRAPHY GUIDE SYSTEM AND METHOD

(71) Applicant: Joo Young Oh, Seoul (KR)

(72) Inventor: Joo Young Oh, Seoul (KR)

(73) Assignee: Joo Young Oh, Seoul (KR)

( * ) Notice: Subject to any disclaimer, the term of this patent is extended or adjusted under 35 U.S.C. 154(b) by 100 days.

(21) Appl. No.: 16/092,541

(22) PCT Filed: Nov. 22, 2017

(86) PCT No.: PCT/KR2017/013349
§ 371 (c)(1),
(2) Date: Oct. 10, 2018

(87) PCT Pub. No.: WO2018/097596
PCT Pub. Date: May 31, 2018

(65) Prior Publication Data
US 2019/0125291 A1    May 2, 2019

(30) Foreign Application Priority Data

Nov. 22, 2016   (KR) .................. 10-2016-0155569

(51) Int. Cl.
*A61B 6/00* (2006.01)
*H04N 5/445* (2011.01)
(Continued)

(52) U.S. Cl.
CPC ............ *A61B 6/545* (2013.01); *A61B 5/0035* (2013.01); *A61B 5/0077* (2013.01); *A61B 6/463* (2013.01);
(Continued)

(58) Field of Classification Search
CPC .............. G06T 2210/41; G06T 7/0014; G06T 2207/10016; G06T 2207/30036; G06T 2207/30196
See application file for complete search history.

(56) References Cited

U.S. PATENT DOCUMENTS 7,346,145 B2 * 3/2008 Yoneyama ............... A61B 6/00
378/82
7,489,759 B2 * 2/2009 Beyrard ............... A61B 6/4429
378/25
(Continued)

FOREIGN PATENT DOCUMENTS

JP    2011-024721 A    2/2011
JP    2012-254286 A    12/2012
(Continued)

OTHER PUBLICATIONS

International Search Report for PCT/KR2017/013349 dated Feb. 13, 2018.

*Primary Examiner* — Yosef Kassa
(74) *Attorney, Agent, or Firm* — The PL Law Group, PLLC

(57) ABSTRACT

A radiography guide system includes a patient image providing unit for providing, on a screen, one piece of information among information on the position where a virtual patient is to be placed, a radiographic direction, and a radiographic angle, and a patient image which represents, as a three-dimensional image, the virtual patient's posture corresponding to a viewing angle, and an overlay image providing unit for generating an external image which represents, as a three-dimensional image, the appearance of the virtual patient's body according to the position information, the radiographic direction, and the radiographic angle, an internal image which represents the skeleton structure of the body as a three-dimensional image, and a radiographic
(Continued)

image of the body. The overlay image providing unit provides, on the screen, an overlay image which overlappingly represents the internal image, the external image, and the radiographic image in the state where the images are registered.

20 Claims, 28 Drawing Sheets

(51) Int. Cl.
    *A61B 5/00*     (2006.01)
    *G16H 30/40*     (2018.01)
    *H04N 5/232*     (2006.01)
    *G09G 5/377*     (2006.01)
    *G06F 3/0484*     (2013.01)

(52) U.S. Cl.
    CPC ............... *A61B 6/466* (2013.01); *A61B 6/58* (2013.01); *G09G 5/377* (2013.01); *G16H 30/40* (2018.01); *H04N 5/232* (2013.01); *H04N 5/44504* (2013.01); *A61B 6/469* (2013.01); *G06F 3/04845* (2013.01); *G06F 2203/04804* (2013.01); *G09G 2340/12* (2013.01); *G09G 2380/08* (2013.01)

(56) References Cited

U.S. PATENT DOCUMENTS

| | | | | |
|---|---|---|---|---|
| 7,508,388 B2* | 3/2009 | Barfuss | ............... | A61B 6/466 |
| | | | | 345/418 |
| 8,023,306 B2* | 9/2011 | Sargent | ............... | B82Y 10/00 |
| | | | | 257/9 |
| 8,326,011 B2* | 12/2012 | Star-Lack | ............ | G06T 7/0012 |
| | | | | 378/7 |
| 8,908,826 B2* | 12/2014 | Bernhardt | ............. | A61B 6/022 |
| | | | | 378/42 |
| 9,001,961 B2* | 4/2015 | Star-Lack | ............ | A61B 6/032 |
| | | | | 378/7 |
| 2013/0051523 A1 | 2/2013 | Davydov et al. | | |
| 2016/0213329 A1 | 7/2016 | Dirkes | | |

FOREIGN PATENT DOCUMENTS

| | | |
|---|---|---|
| JP | 2016-034300 A | 3/2016 |
| KR | 10-2008-0109379 A | 12/2008 |
| KR | 10-2009-0077019 A | 7/2009 |
| KR | 10-2013-0103689 A | 9/2013 |
| KR | 10-2014-0020124 A | 2/2014 |
| KR | 10-2014-0060808 A | 5/2014 |
| WO | WO 2007/129493 A1 | 11/2007 |

* cited by examiner

Region
- Skull, Foramen ovale, Spinosum foramen
Pathology
- Skull, Inflammation state of sphenoidal sinus and ethmoid sinus, Traumatic disease Camera image Guiding image 1

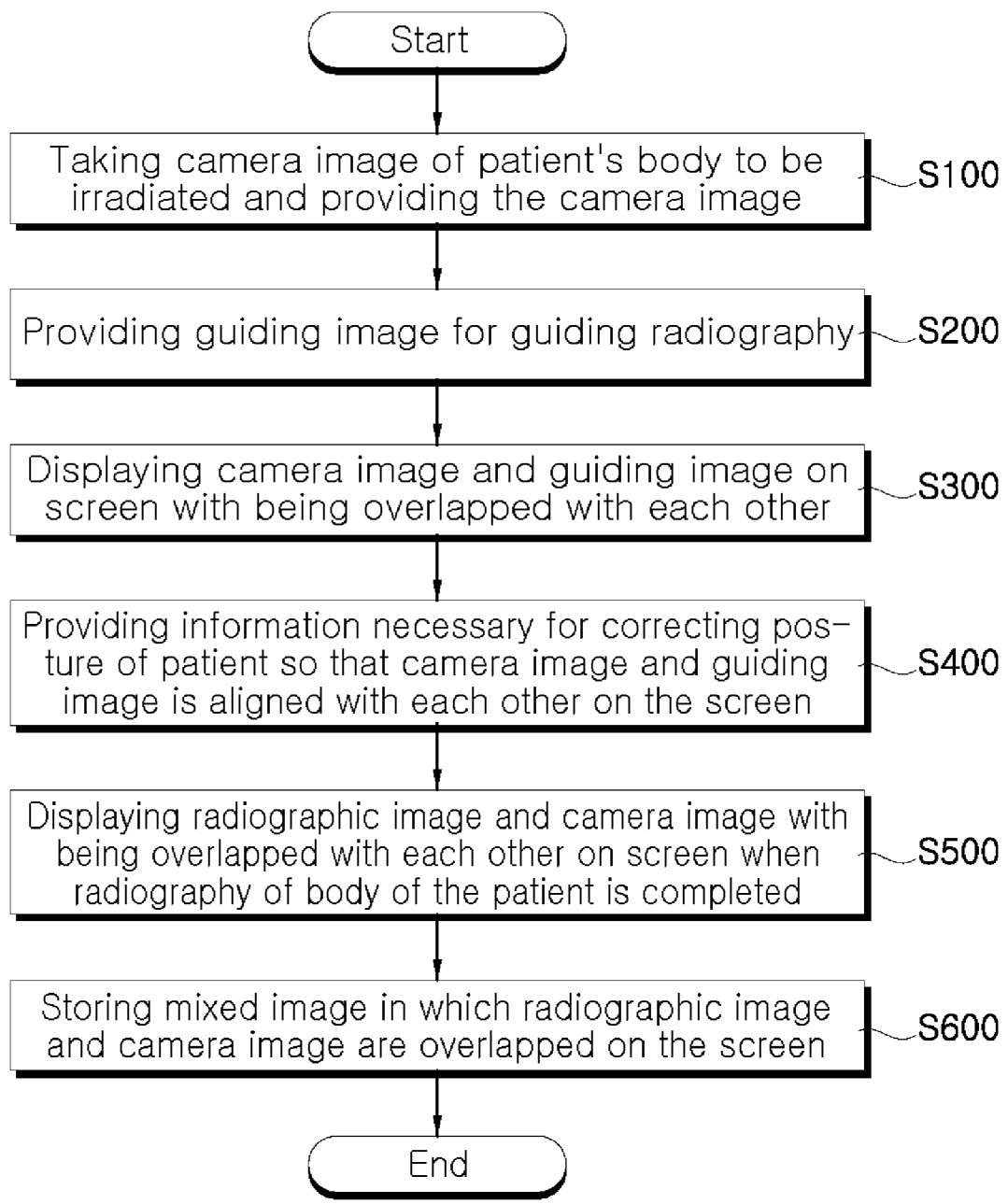

RADIOGRAPHY GUIDE SYSTEM AND METHOD

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2017/013349, filed Nov. 22, 2017, which claims priority to the benefit of Korean Patent Application No. 10-2016-0155569 filed in the Korean Intellectual Property Office on Nov. 22, 2016, the entire contents of which are incorporated herein by reference.

TECHNICAL FIELD

The invention relates to a radiography guiding system and method. More particularly, the invention relates to a radiography guiding system and method using a camera image capable of displaying the camera image and a radiographic image being overlapped and aligned with each other.

BACKGROUND ART

Radiography is a necessary medical technique to quickly and reliably identify a patient's condition, but it is also a dangerous technique that applies a certain amount of harm to the patient's body when used. Accurate and safe radiography and understanding of radiographic images one of the greatest tasks of a radiologist, and it is the reason why the radiologist needs national license. The understanding of accurate radiography can contribute to significantly reducing failure of the radiography and reducing retake of radiography.

General radiography is the most basic technology of radiologists and the area where the most radiation workers work. In addition, the general radiography also takes up a large portion of the national radiation examination. However, since a radiographic image shows only a specific region photographed in a combination of black and white, it is generally difficult to understand why the radiographic image appears as such a structure.

Since only outside of the body can be seen in our eyes, learners who study radiography should learn by imagining inside of the body that is not seen. It is very difficult for an educator to clarify changes of an anatomical structure according to the body posture. Most of them depend on the imagination of the learner to understand the radiography accurately. Also, even for experienced radiologists, it is not easy to memorize more than 200 types of general radiography techniques completely. It is a reality to find necessary test method from a radiation book of considerable thickness.

Accordingly, the present inventor has developed a method and system for easily understanding and acquiring radiography through three-dimensional images and easily viewing and confirming various radiographic techniques.

SUMMARY

The present invention provides a three-dimensional image display method, a radiography guiding system using the three-dimensional image and a method thereof to easily understand radiography by the three-dimensional image and to easily view and check various radiography technologies.

To solve these problems, a radiography guiding system is provided. The radiography guiding system includes a patient image provider to provide a patient image, which is a 3-D image of a posture of a virtual patient corresponding to a viewing angle with an information of one of location information on which the virtual patient is to be located, a radiographic direction and angle of radiography, on a screen, and an overlay image provider to generate an external image which is a 3-D image of an external appearance of a body of the virtual patient corresponding to the location information, the radiographic direction and the angle of radiography, an internal image which is 3-D image of a skeletal structure of the body, and a radiographic image of the body. The overlay image provider provides an overlay image, in which the internal image, the external image, and the radiographic image are overlapped and aligned with each other, to the screen.

In an example embodiment, at least one of the external image, the internal image, and the radiographic image may be configured to change its transparency.

In an example embodiment, the transparency may be changed when a button provided on the screen is pressed, a scroll bar is moved, the screen is tapped, or the screen is dragged.

In an example embodiment, the radiography guiding system may further include a medical information provider which can enlarge the radiographic image, and provides medical information on a main anatomical location of the radiographic image.

In an example embodiment, the radiography guiding system may further include an image and description provider which provides a description of the overlay image.

In an example embodiment, the description may include at least one or more of classification of radiography, title of radiography, target location of radiography, size of a cassette, photographing distance, photographing center point, the patient's breathing state, posture adjustment of the patient, radiation field, evaluation of the radiographic image, tube voltage, tube current and radiographic tip.

In an example embodiment, the radiography guiding system may further include a test method provider which provides a test method associated with radiography and important test parameters related to the test method.

In an example embodiment, the radiography guiding system may further include a terms provider which provides an image of the skeletal structure of the body and anatomical names constituting the skeletal structure.

In an example embodiment, the radiography guiding system may further include a list provider which provides a list of radiographic techniques for each of the anatomical names.

In an example embodiment, the radiography guiding system may further include a search provider which provides search function about radiography techniques.

In an example embodiment, the radiography guiding system may further include a camera part which photographs a body part of the patient, and a real-time overlay image provider which overlays the overlay image provided by the overlay image provider and a camera image provided by the camera part on the screen.

In addition, to solve these problems, a radiography guiding system is provided. The radiography guiding system includes a camera part which photographs a body of a patient, who is irradiated by radiation, and provides a camera image which is photographed, a guiding image provider which provides a guiding image for guiding radiography, an overlay image provider which displays the camera image and the guiding image being overlapped with each other on a screen, and an information provider which provides information necessary for correcting a posture of the patient so that the camera image and the guiding image are aligned with each other on the screen.

In an example embodiment, the camera part may be arranged to face a direction in which the radiation is incident.

In an example embodiment, the guide image may include at least one of an image of a skeletal structure representing the body of the patient and an image of an outline of the body of the patient.

In an example embodiment, the overlay image provider may display a radiographic image and the camera image with being overlapped with each other on the screen when the radiography of the body of patient is completed.

In an example embodiment, at least one of the camera image, the guiding image, and the radiographic image may be configured to change its transparency.

In an example embodiment, the transparency may be changed when a button provided on the screen is pressed, a scroll bar is moved, the screen is tapped, or the screen is dragged.

In an example embodiment, the information necessary for correcting the posture of the patient may include at least one or more of a unique number of the patient, name of the patient, gender, age, current angle of the radiation emitted from x-ray tube, reference angle of the radiation for accurate radiography, evaluation of the current angle, a current distance between a radiation detector and the patient, reference distance for accurate radiography and evaluation of the current distance.

In addition, to solve these problems, a radiography guiding method is provided. The radiography guiding method includes taking a camera image of a body of patient to be irradiated and providing the camera image, providing a guiding image for guiding radiography, displaying the camera image and the guiding image on a screen with being overlapped with each other, and providing an information necessary for correcting a posture of the patient so that the camera image and the guiding image is aligned with each other on the screen.

In an example embodiment, the radiography guiding method may further include displaying a radiographic image and the camera image with being overlapped with each other on the screen when the radiography of the body of the patient is completed.

According to the radiography guiding system and method according to the present invention, since the structure of the radiographic image which was difficult to understand through conventional radiography related books and the accurate posture of the patient can be obtained at a glance through the overlay technique of the three-dimensional images, learner's understanding of radiography is greatly improved.

In addition, according to the radiography guiding system and method according to the present invention, the learner learning the radiography can understand the radiography in an easy-to-understand way through the three-dimensional image.

In addition, according to the radiography guiding system and method according to the present invention, it contains all the image information for various radiography, so that it is possible to replace a thick book for learning the radiography and to easily search the contents of the radiography.

In addition, according to the radiography guiding system and method according to the present invention, the posture of the patient can be adjusted so that the posture of the patient is correct during actual radiography, the patient can be taken radiograph in correct posture.

BRIEF DESCRIPTION OF DRAWINGS

FIG. 32 is a flow chart to explain a radiography guiding method according to still another embodiment of the present invention.

DETAILED DESCRIPTION

Figure 1:
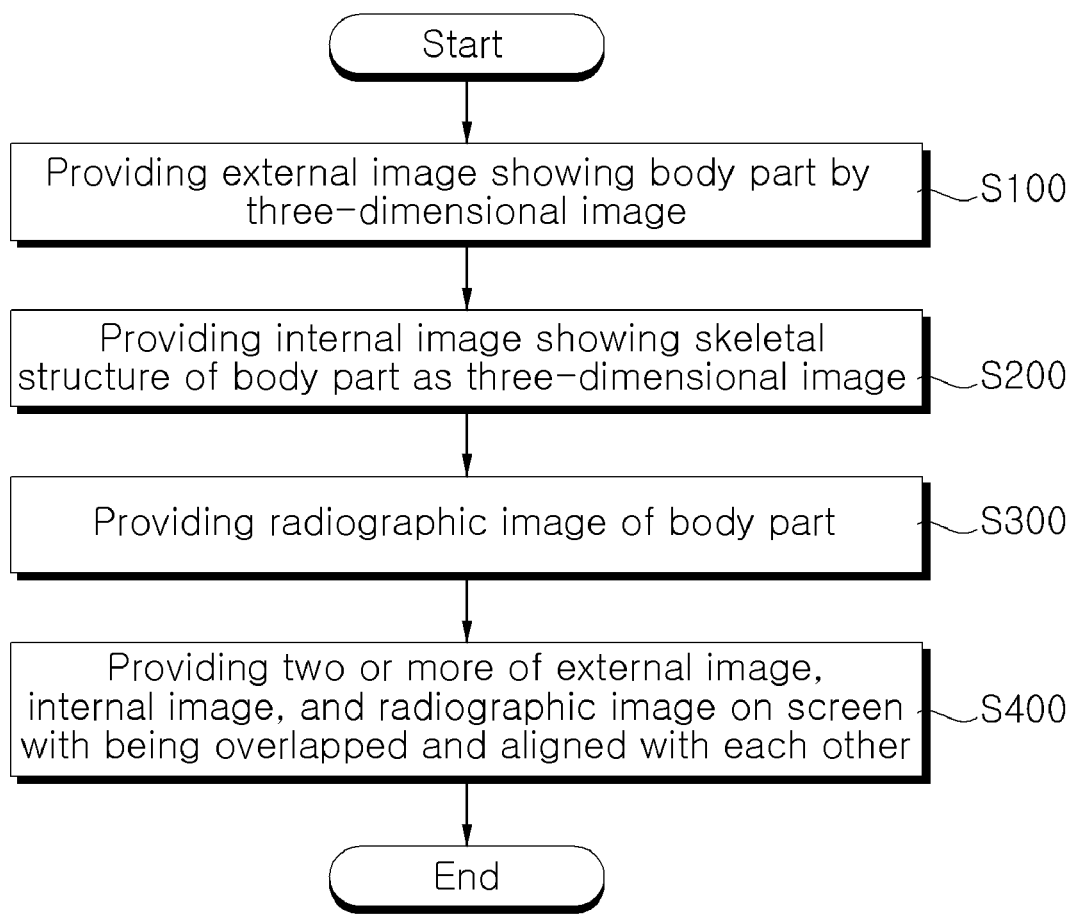
FIG. 1 is a flow chart illustrating a radiography guiding method according to an example embodiment of the present invention.
Figure 2:
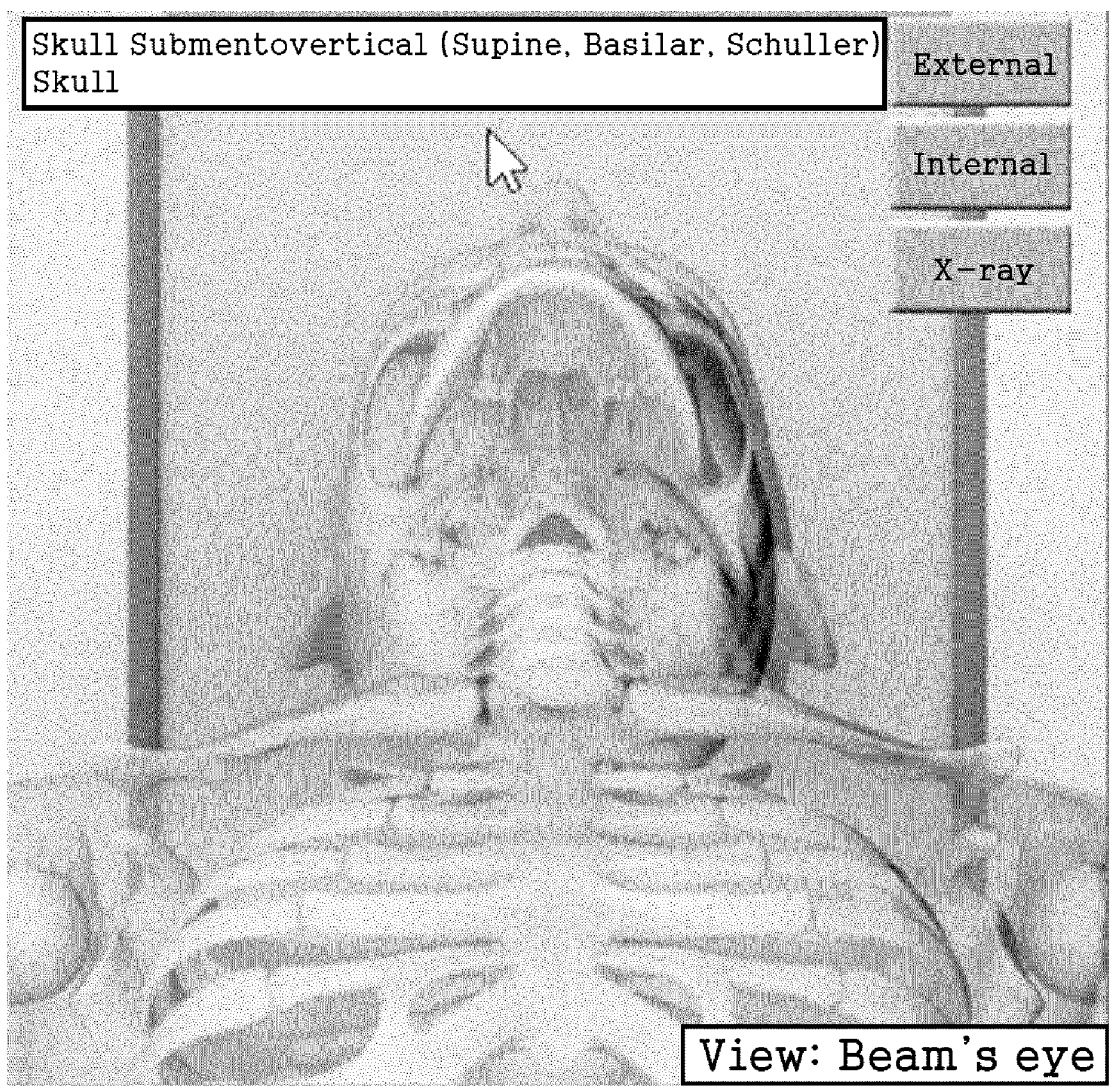
FIGS. 2 to 5 are pictures to explain a process in which a transparency of an external image is changed when the external image and an internal image are provided to be overlapped with each other.

Hereinafter, the invention will be explained in detail with reference to the accompanying drawings. The present invention may, however, be embodied in many different forms and should not be construed as limited to the example embodiments set forth herein and shown in accompanying drawings. The same reference numerals will be used to refer to the same or like parts.

FIG. 1 is a flow chart illustrating a radiography guiding method according to an example embodiment of the present invention. FIGS. 2 to 5 are pictures to explain a process in which a transparency of an external image is changed when the external image and an internal image are provided to be overlapped with each other. FIGS. 6 to 9 are pictures to explain a process in which transparencies of an external image and a radiographic image are changed when the external image and the radiographic image are provided to be overlapped with each other.

Referring to FIGS. 1 to 9, a radiography guiding method according to an embodiment of the present invention includes providing an external image showing a body part by a three-dimensional image (S100), providing an internal image showing a skeletal structure of the boy part as a three-dimensional image (S200), providing a radiographic image of the body part (S300), providing two or more of the external image, the internal image, and a radiographic image which are overlapped and aligned with each other on a screen (S400).

An external image showing a body part by a three-dimensional image is provided (S100). The external image showing the body part by the three-dimensional image is a three-dimensional image of a patient's skin when viewed from the outside. It means that an appearance of the body part of the patient is displayed as a three-dimensional image.

An internal image showing a skeletal structure of the body part as a three-dimensional image is provided (S200). The skeletal structure of the body part may be a skeletal structure positioned inside the body corresponding to the body part appearing in the external image. The internal image may be provided with the external image or may be provided separately.

A radiographic image of the body part may be provided (S300). The radiographic image means a radiographic image of the body part which is in the external image. The radiographic image may be an image corresponding to the body part in the external image. Steps S100 to S300 are not limited to the order described, and the order of each step may be changed.

In an embodiment of the invention, providing of the external image, the internal image and the radiographic image means to be displayed on the screen, or means preparatory work (e.g., pre-storing the external images, the internal images and the radiographic images, etc.) for displaying the external, internal and radiographic images on the screen. For example, the external image, the internal image, and the radiographic image may be stored in advance as images corresponding to various radiography methods.

After the above process, two or more of the external image, the internal image, and the radiographic image are provided on the screen with being overlapped and aligned with each other (S400). As providing two or more of the external image, the internal image, and the radiographic image on the screen with being overlapped and aligned with each other, a learner studying radiography can check at a glance the appearance of the body part, the skeletal structure, and the radiographic image of the body part. For this, one or more of the external image, the internal image, and the radiographic image may be configured such that its transparency can be changed.

Referring to FIGS. 2 to 5, in a state where the skeletal structure of the body part is shown by providing of the internal image, the appearance of the body part by providing of the external image is increasingly shown. By changing the transparency of the external image, the learner can confirm the body part corresponding to the skeletal structure at a glance.

Referring to FIGS. 6 to 9, in a state where the skeletal structure for the body part is provided by the provision of an internal image, the radiographic image of the body part by providing of the radiographic image gradually appears with being overlapped with the skeletal structure. Through the change of the transparency, it is possible to match the radiographic image and the skeletal structure corresponding to the radiographic image at a glance, so that the learner can easily identify that the radiographic image represents which part of the skeletal structure.

For example, the change of the transparency can be operated by pressing a button provided on the screen, moving a scroll bar provided on the screen, tapping the screen, or dragging the screen. For reference, a display panel having a touch function may be used to change transparency when a screen is tapped.

Figure 10:
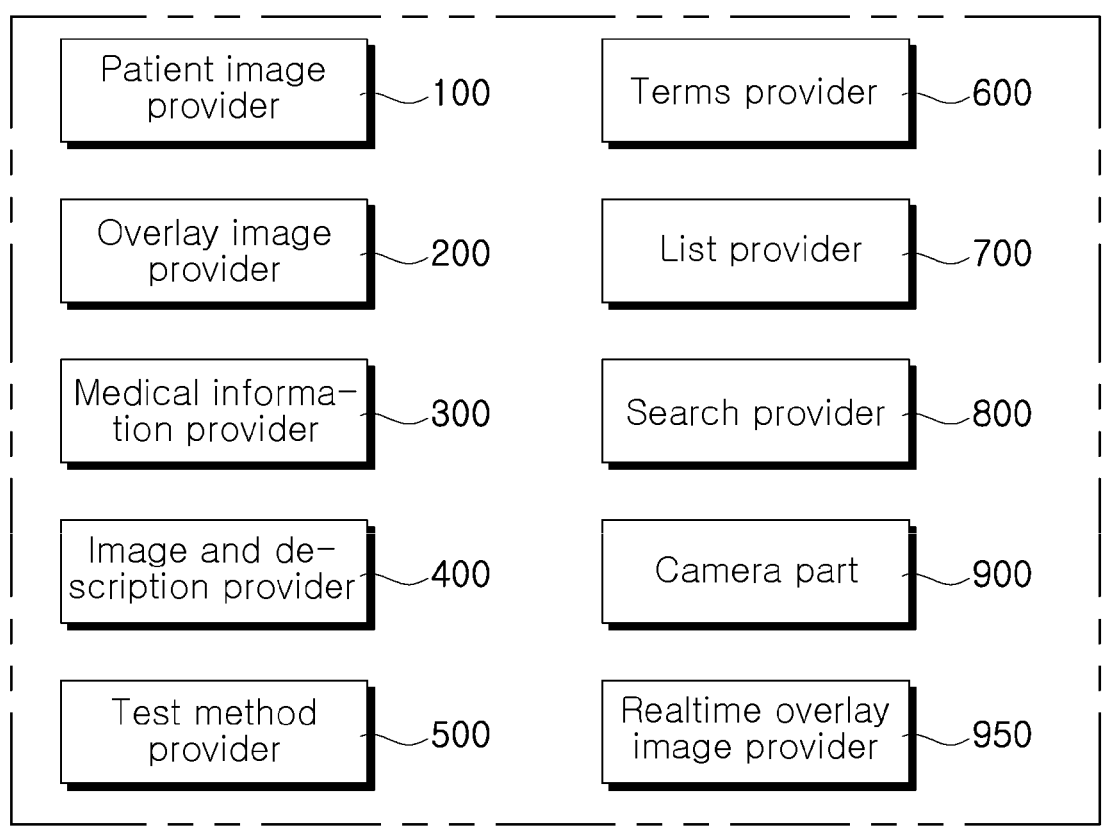
FIG. 10 is a view to explain a radiography guiding system according to an embodiment of the present invention.
Figure 11:
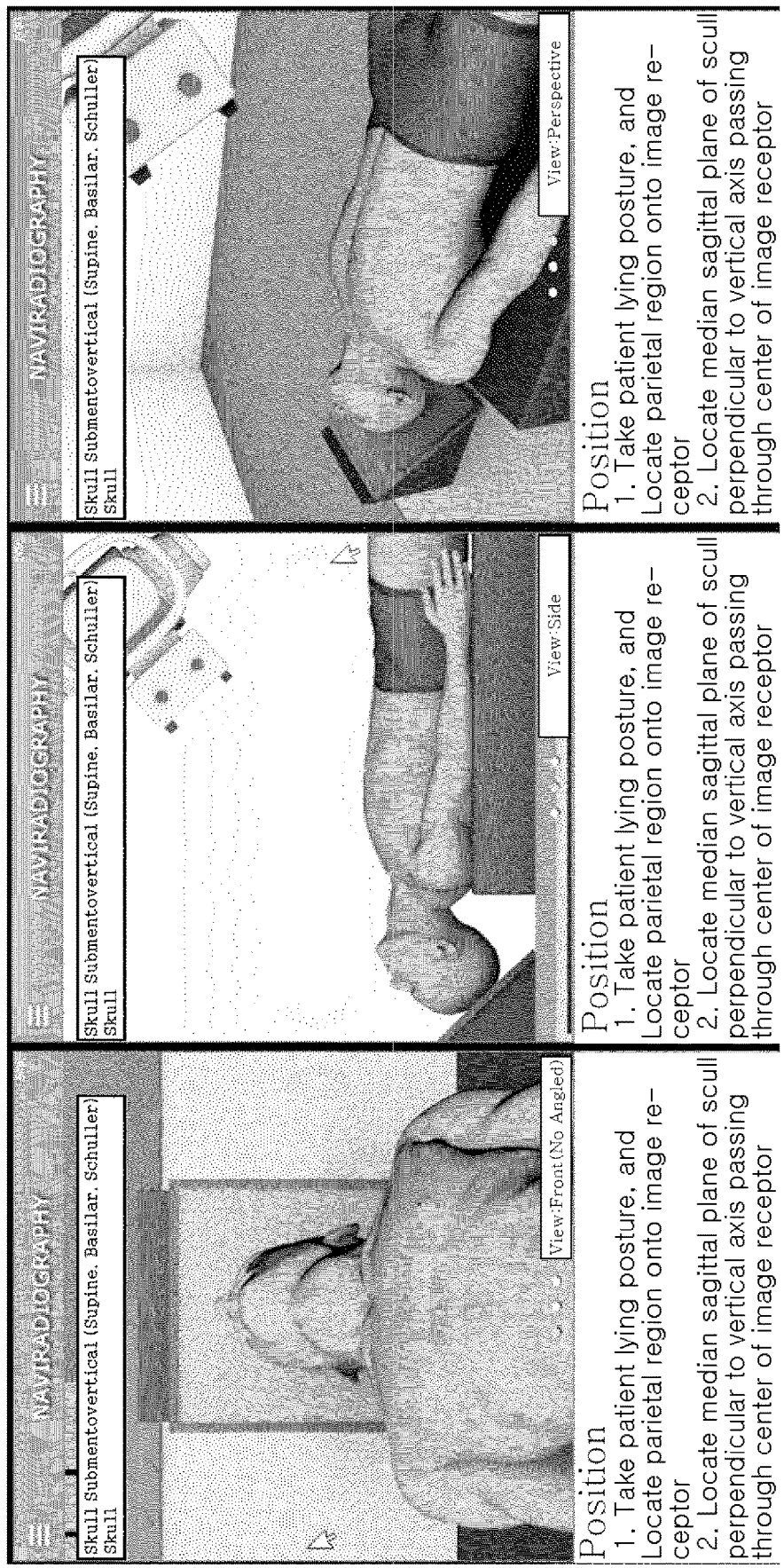
FIG. 11 is a picture to explain a patient image provider according to an embodiment of the present invention.
Figure 12:
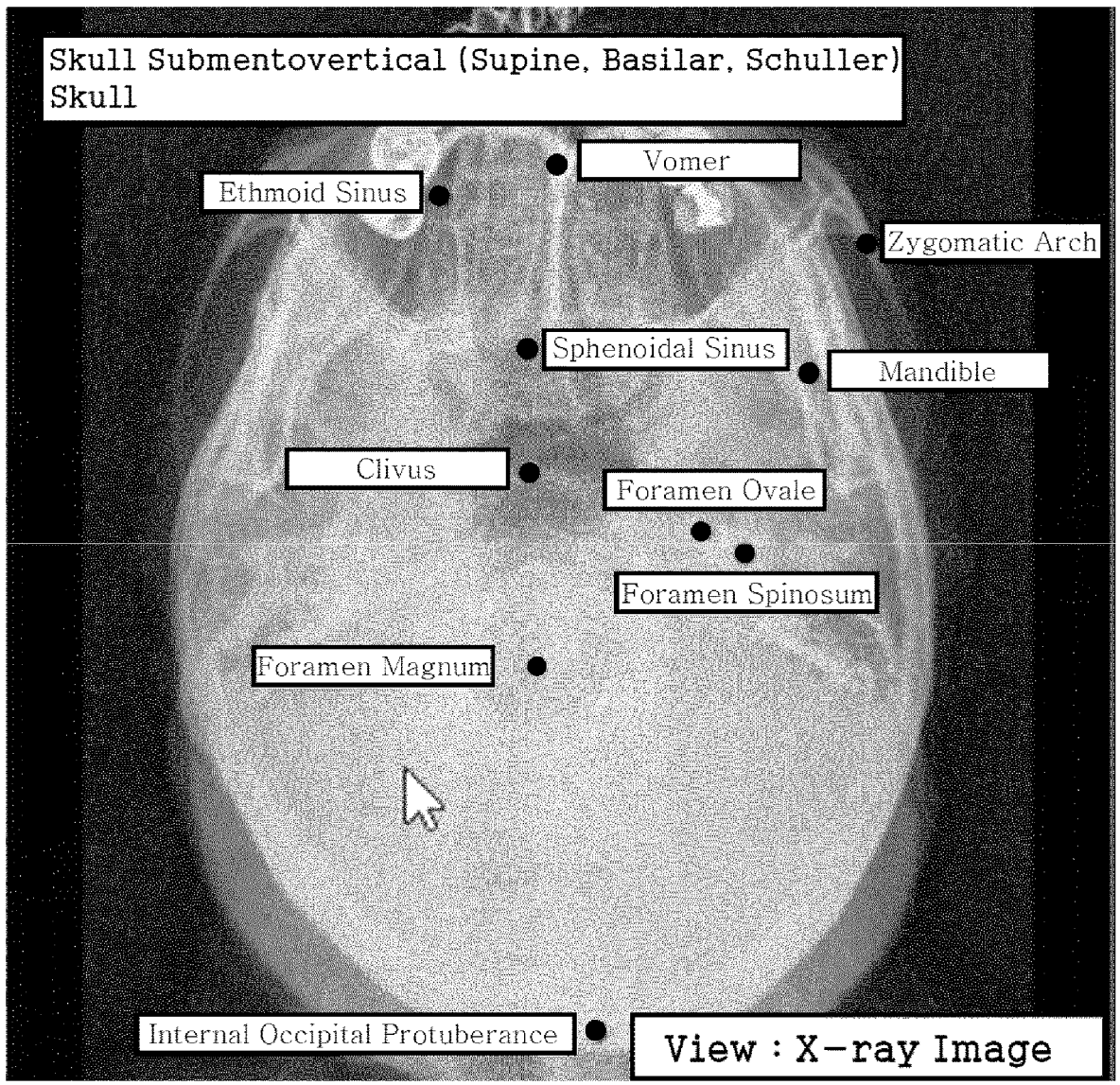
FIG. 12 is a picture to explain a medical information provider according to an embodiment of the present invention.
Figure 13:
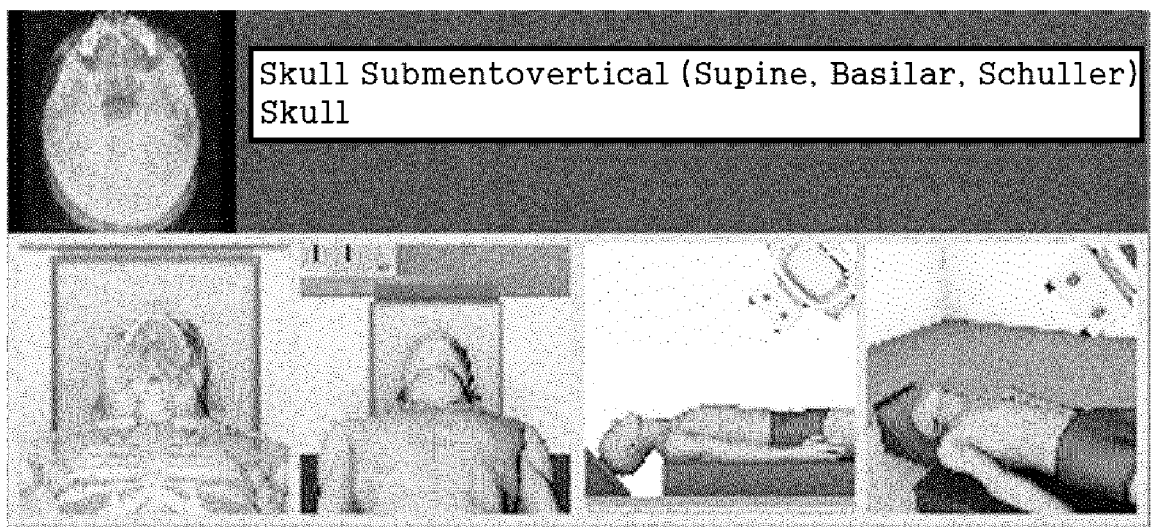
FIG. 13 is a picture to explain an image and description provider according to an embodiment of the present invention.
Figure 14:
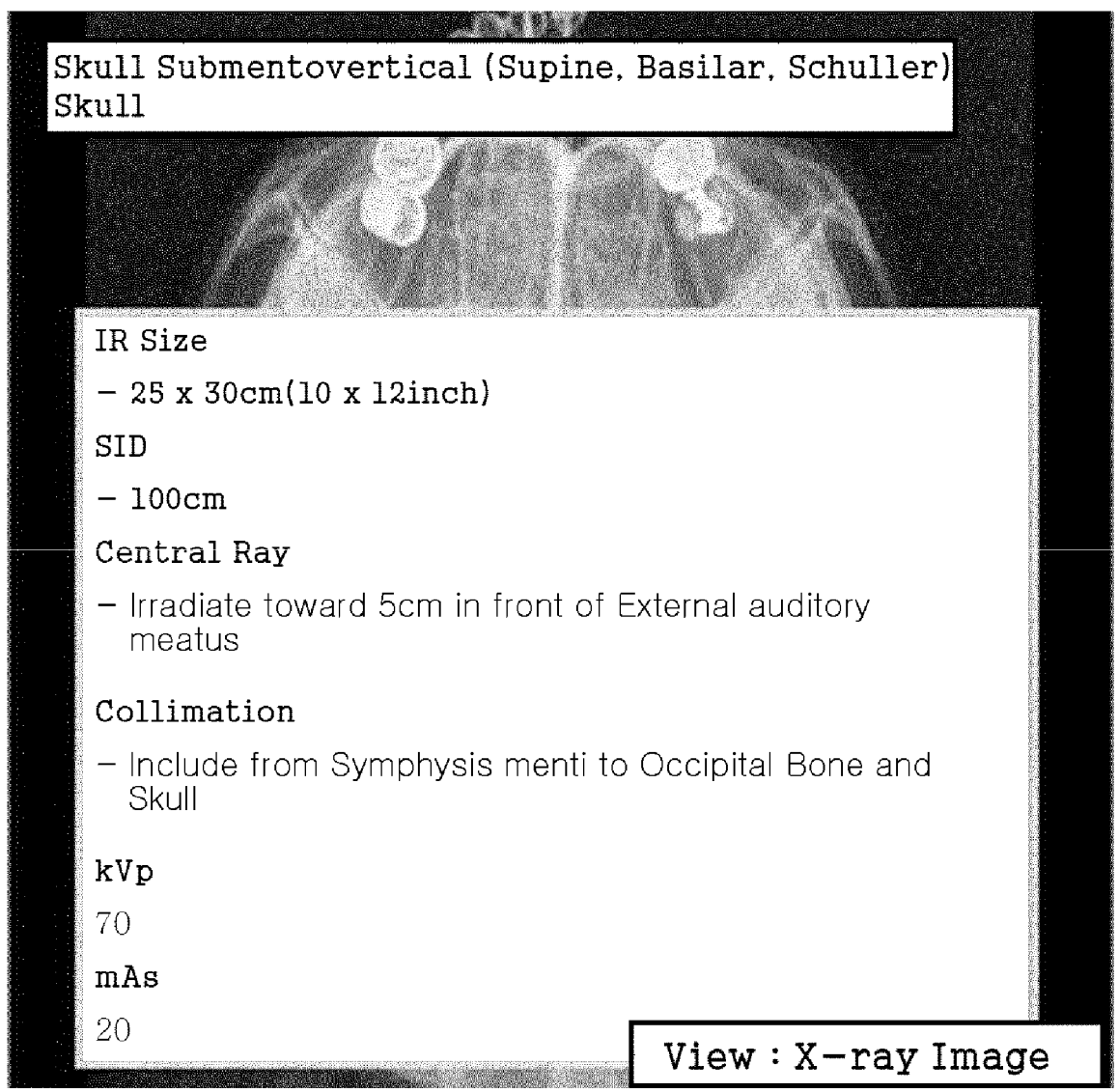
FIG. 14 is a picture to explain a test method provider according to an embodiment of the present invention.
Figure 15:
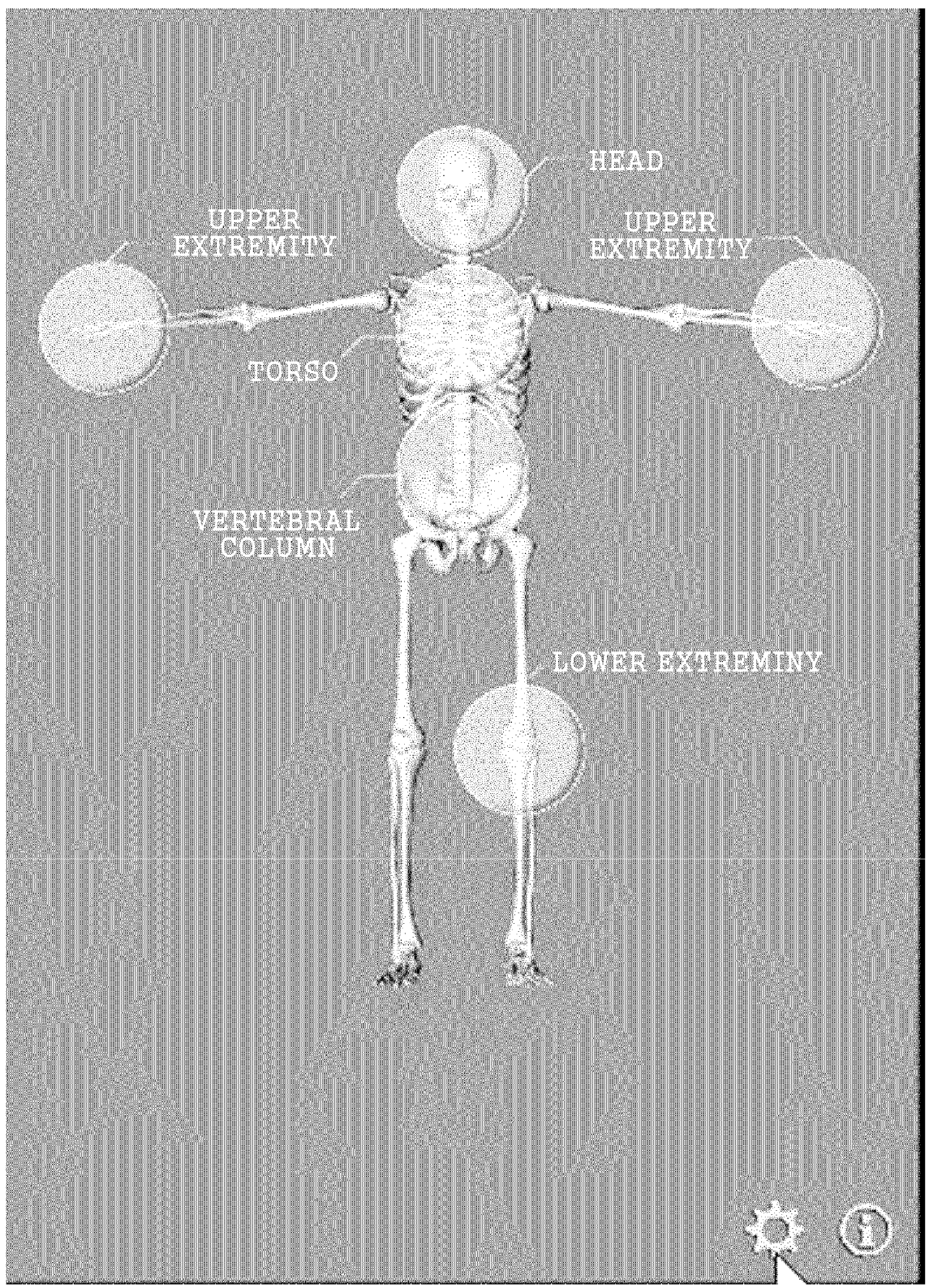
FIG. 15 is a picture to explain a terms provider according to an embodiment of the present invention.
Figure 16:
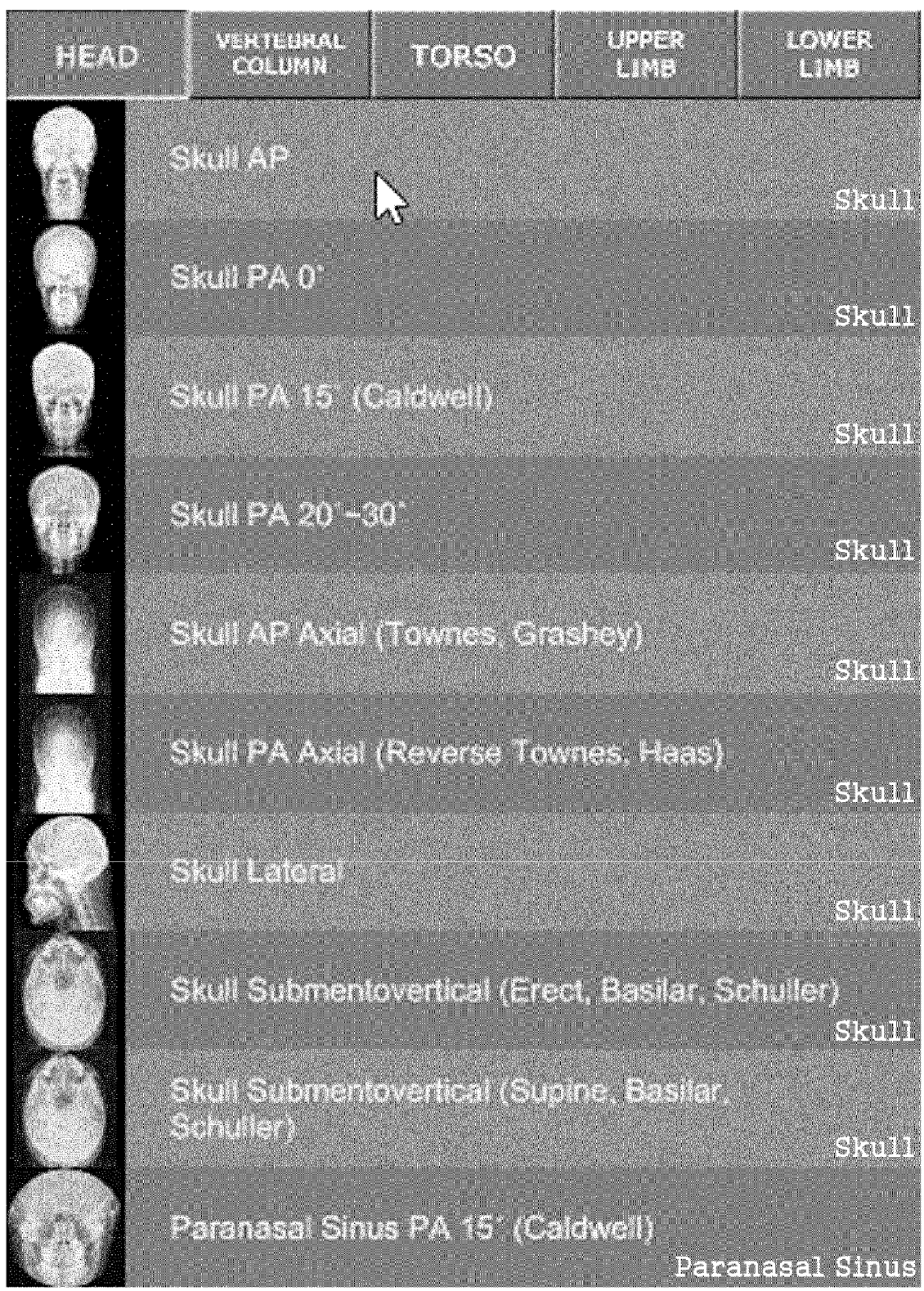
FIG. 16 is a picture to explain a list provider according to an embodiment of the present invention.
Figure 17:
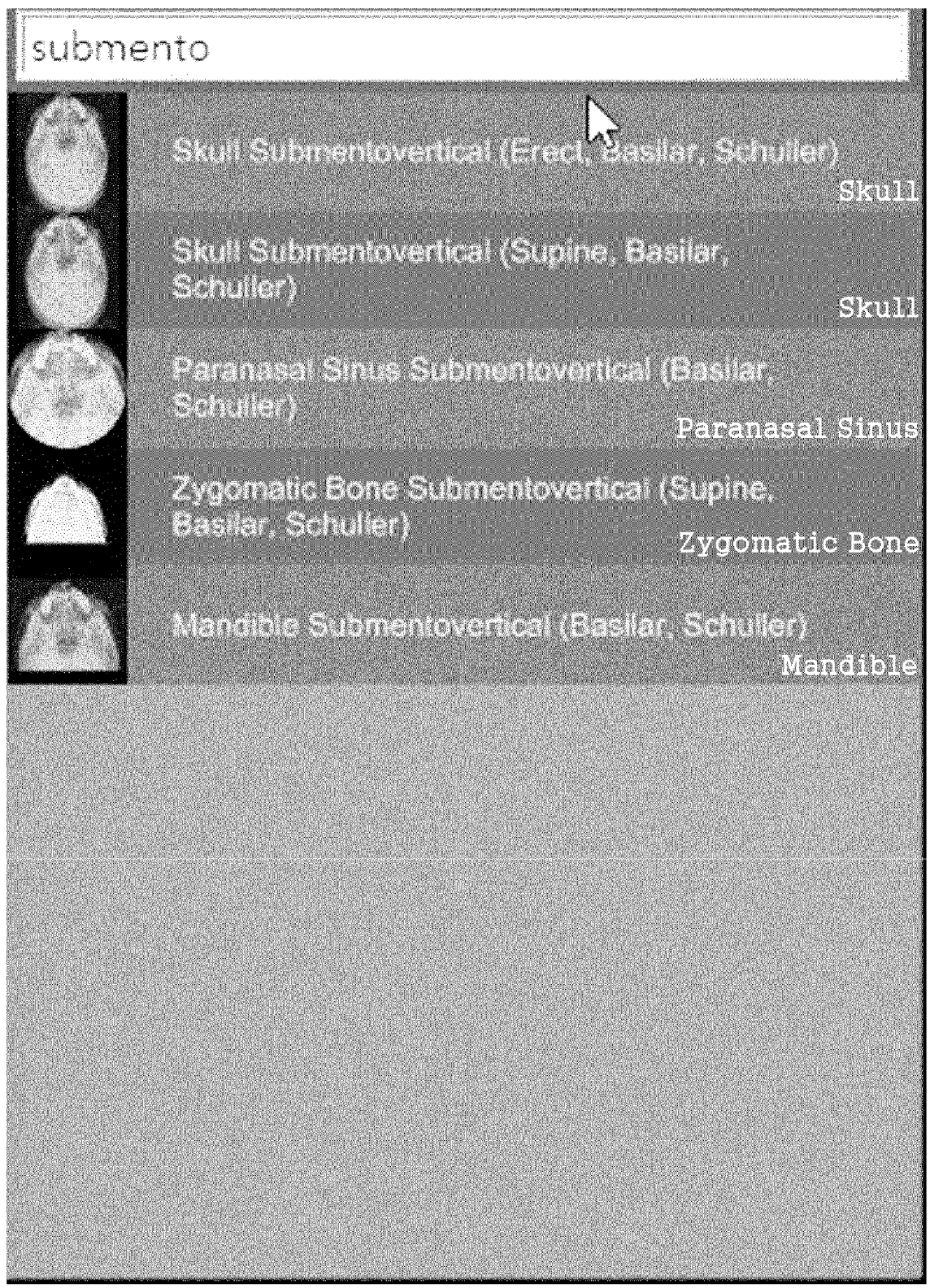
FIG. 17 is a picture to explain a search provider according to an embodiment of the present invention.
Figure 18:
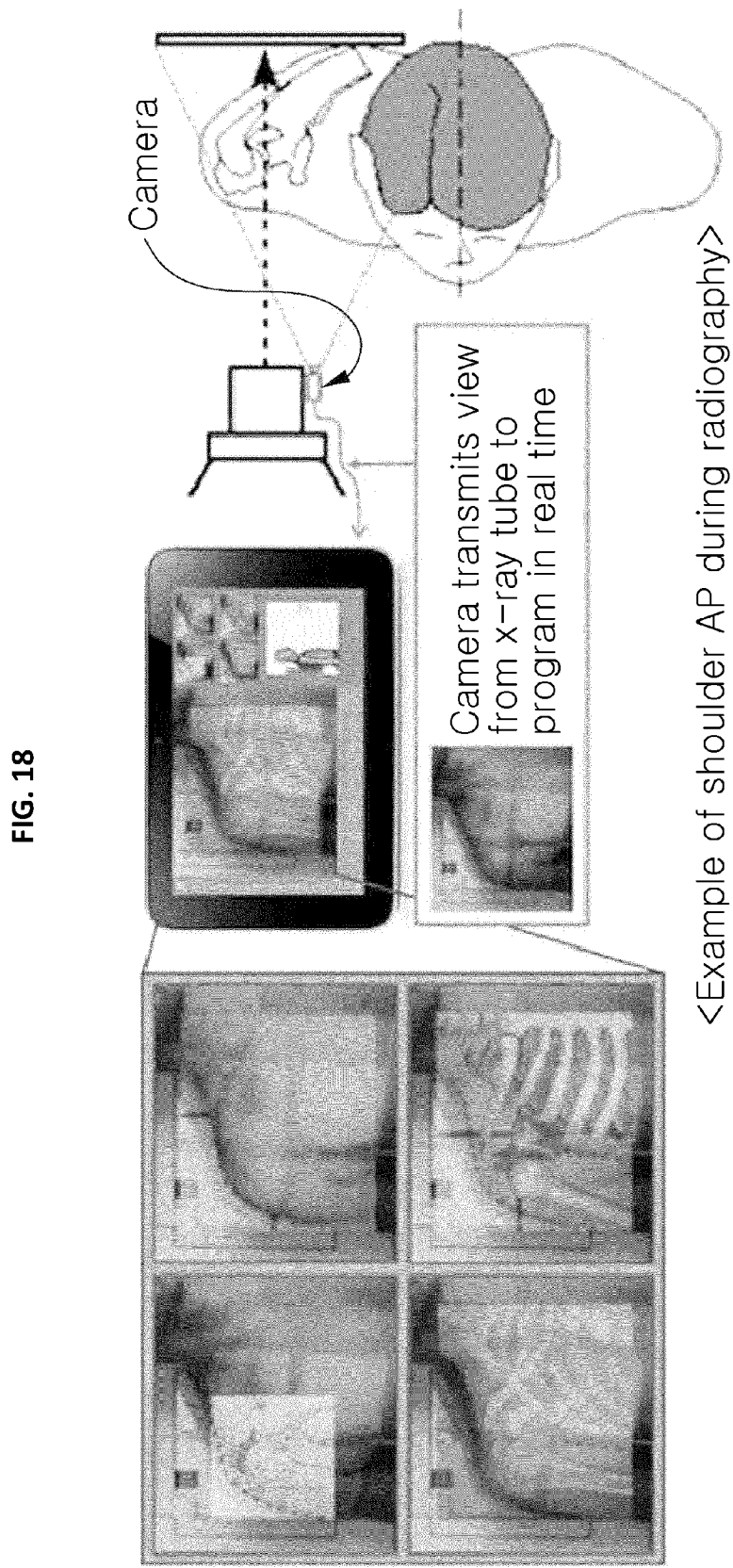
FIG. 18 is a picture to explain providing a real-time overlay image according to an embodiment of the present invention.

FIG. 10 is a view to explain a radiography guiding system according to an embodiment of the present invention. FIG. 11 is a picture to explain a patient image provider according to an embodiment of the present invention. FIG. 12 is a picture to explain a medical information provider according to an embodiment of the present invention. FIG. 13 is a picture to explain an image and description provider according to an embodiment of the present invention. FIG. 14 is a picture to explain a test method provider according to an embodiment of the present invention. FIG. 15 is a picture to explain a terms provider according to an embodiment of the present invention. FIG. 16 is a picture to explain a list provider according to an embodiment of the present invention. FIG. 17 is a picture to explain a search provider according to an embodiment of the present invention. FIG. 18 is a picture to explain providing a real-time overlay image according to an embodiment of the present invention.

Referring to FIG. 10, a radiography guiding system 1000 according to an example embodiment of the present invention includes an overlay image provider 200, and may further include at least one or more of a patient image provider 100, a medical information provider 300, an image and description provider 400, a test method provider 500, a terms provider 600, a list provide 700, a search provider 800, a camera part 900 and a real-time overlay image provider 950.

First, the overlay image provider 200 provides an external image which is a 3-D image of an external appearance of a portion of a body of a virtual patient, provides an internal image which is 3-D image of a skeletal structure of the body of the virtual patient, and provides a radiographic image of the body of the virtual patient. The overlay image provider 200 provides at least two or more of the external image, the internal image, and the radiographic image being overlapped with each other and aligned with each other on a screen.

The patient image provider 100 may provide a patient image, which is represented by a three-dimensional image according to viewing angle of the virtual patient. In addition, the patient image provider 100 may further provide one of a radiographic direction for radiography, angle of radiography and location information on which the patient is to be located in a radiography device for radiography. Referring to FIG. 11, when radiography of a head bone is required, it can be confirmed that the location information on which the patient is to be located, the direction for radiography and the three-dimensional image of the patient according to viewing angle are displayed together. In this case, the viewing angle can be expressed in various ways, such as front, side, and perspective.

The medical information provider 300 may enlarge the enlarge the radiographic image, and provides medical information on a main anatomical location of the radiographic image. Referring to FIG. 12, it can be seen that main anatomical locations of the head bone is displayed along with the radiographic image.

The image and description provider 400 may provide at least one overlay image in which two or more of the virtual patient image, the external image, the internal image, and the radiographic image are overlapped and aligned with each other on the screen is provided with a description. In this case, the description of the image may include at least one or more of classification of radiography, title of radiography, target location of radiography, size of a cassette, photographing distance, photographing center point, the patient's breathing state, posture adjustment of the patient, radiation field, evaluation of the radiographic image, tube voltage, tube current and radiographic tip. Referring to FIG. 13, image of the virtual patient and the overlay image are displayed together with the description of the image.

The test method provider 500 provides a test method associated with radiography and important test parameters related to the test method. Referring to FIG. 14, it can be seen that the parameters related to the radiography are displayed when radiography of the head bone is performed.

The terms provider 600 may provide an image of the skeletal structure of the body and anatomical names constituting the skeletal structure. Referring to FIG. 15, it can be seen that the image of the skeletal structure of the body and anatomical names constituting the skeletal structure are displayed corresponding to the body part. Here, a list of the radiographic techniques for the body part may be displayed on the screen when the body part marked with the anatomical name is clicked.

The list provider 700 provides a list of radiographic techniques for each of the anatomical names. Referring to FIG. 16, it can be seen that the list of radiographic techniques for anatomical names (such as Head, Vertebral column, Torso and the like) is displayed. Here, when one of the radiography techniques displayed in the list is selected, information related to the selected radiography technique (external image, internal image, overlay image, etc.) can be displayed.

The search provider 800 provides search function about radiography techniques. For example, it is possible to search for a radiographic technique through a method of providing a search window. Referring to FIG. 17, when 'submento' is typed in the search window, a list of radiographic techniques including 'submento' may be displayed. Here, when one of the radiography techniques displayed in the list is selected, information related to the selected radiography technique (external image, internal image, overlay image, etc.) can be displayed.

The camera part 900 photographs the body part of the patient. In this case, the camera part 900 may be arranged toward a direction of looking the body part of the patient from the x-ray tube of the radiography device. In order to overlap and align with the overlay image, the image of the body part of the patient to be photographed through the camera part 900 may be adjusted in terms of the size of the image, the distance and position of the camera part 900 to photograph the body part of the patient.

The real-time overlay image provider 950 provides the overlay image provided by the overlay image provider and a camera image provided by the camera part with being overlapped with each other on the screen. Referring to FIG. 18, it is seen that the camera image of the body part of the patient photographed through the camera part 900 and the overlay image provided through the video data provider 200 are overlapped with each other on the screen. Therefore, the user can correct the posture of the patient so that the posture of the patient for radiography is correct based on the overlay image. In this case, as shown in FIG. 18, a photographing auxiliary line may be displayed in a form of a red dotted line or the like. The photographing auxiliary line may be used together with the image photographed through the camera part 900 or may be used alone without the image photographed through the camera part 900.

Figure 19:
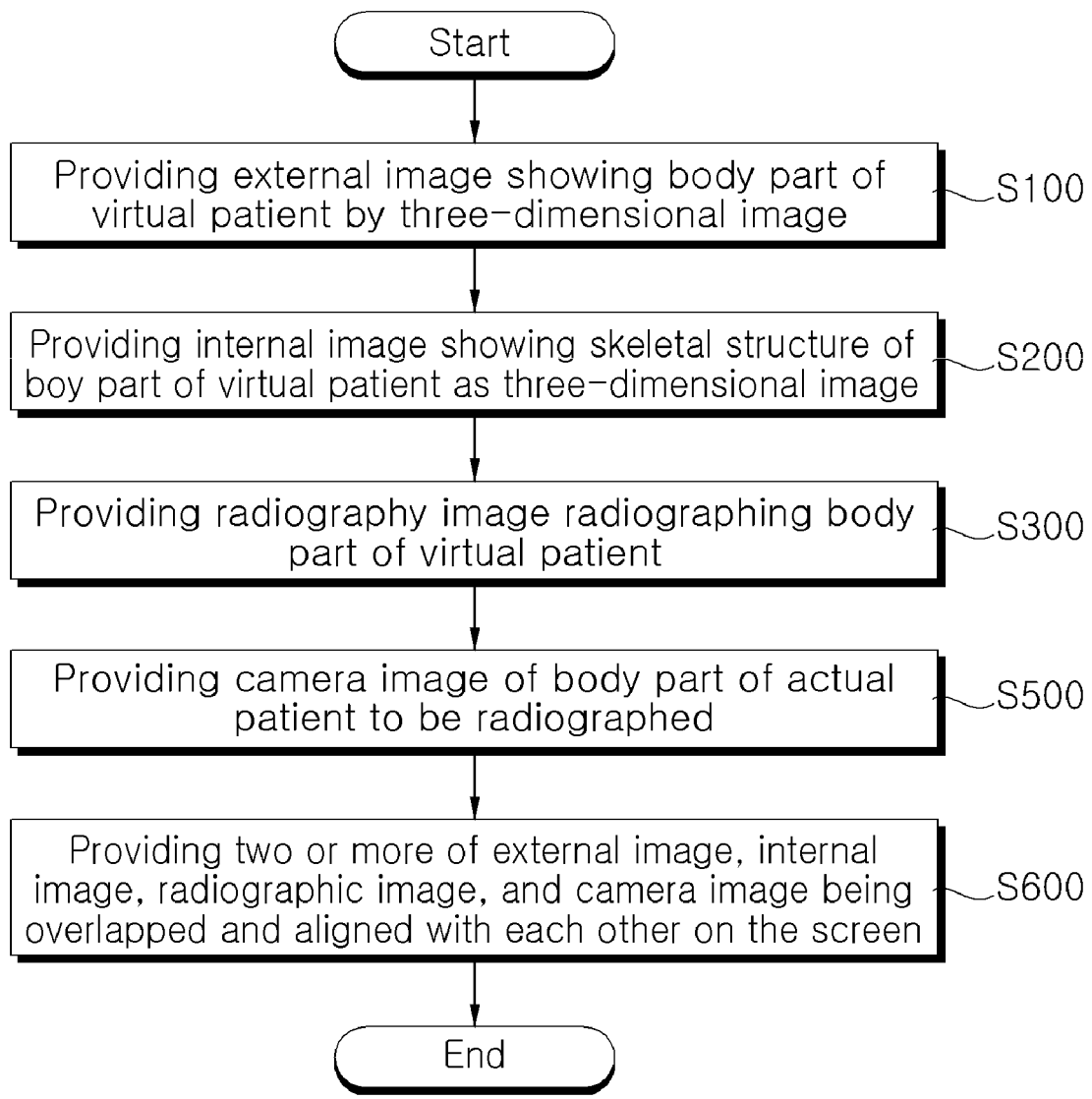
FIG. 19 is a flow chart illustrating a radiography guiding method according to an example embodiment of the present invention.

FIG. 19 is a flow chart illustrating a radiography guiding method according to an example embodiment of the present invention.

Referring to FIG. 19, a radiography guiding method according to an embodiment of the present invention includes providing an external image showing a body part of a virtual patient by a three-dimensional image (S100), providing an internal image showing a skeletal structure of the boy part of the virtual patient as a three-dimensional image (S200), providing a radiography image radiographing the body part of the virtual patient (S300), providing a camera image of a body part of actual patient to be radiographed (s500), providing two or more of the external image, the internal image, the radiographic image, and the camera image being overlapped and aligned with each other on the screen (S600).

First, an external image showing a body part of a virtual patient by a three-dimensional image is provided (S100). The external image showing the body part by the three-dimensional image is a three-dimensional image of the virtual patient's skin when viewed from the outside. It means that an appearance of the body part of the virtual patient is displayed as a three-dimensional image.

An internal image showing a skeletal structure of the boy part of the virtual patient as a three-dimensional image is provided (S200). The skeletal structure of the body part of the virtual patient may be a skeletal structure positioned inside the body corresponding to the body part of the virtual patient appearing in the external image. The internal image may be provided with the external image or may be provided separately.

A radiography image radiographing the body part of the virtual patient is provided (S300). The radiographic image means a radiographic image of the body part of the virtual patient which is in the external image. The radiographic image may be an image corresponding to the body part in the external image.

A camera image of a body part of actual patient to be radiographed is provided (S500). This is a step of photographing a body part of the actual patient in real-time using the camera part 900. In this case, the camera part 900 may be arranged toward a direction of looking the body part of the patient from the x-ray tube of the radiography device. In order to overlap and align with the overlay image, the image of the body part of the patient to be photographed through the camera part 900 may be adjusted in terms of the size of the image, the distance and position of the camera part 900 to photograph the body part of the patient. A photographed image of a body part of the actual patient can be displayed. Meanwhile, order of steps S100 to S400 is not limited thereto, and the order of each step may be changed.

Two or more of the external image, the internal image, the radiographic image, and the camera image being overlapped and aligned with each other on the screen is provided (S600). Referring to FIG. 18, it is seen that the overlay image provided by the overlay image provider 200 and the camera image provided by the camera part 900 are provided with being overlapped and aligned with each other. Therefore, the user can correct a posture of the patient so that the posture of the patient for radiography is correct based on the overlay image. In this case for reference, as shown in FIG. 18, a photographing auxiliary line may be displayed in a form of a red dotted line or the like. The photographing auxiliary line may be used together with the image photographed through the camera part 900 or may be used alone without the image photographed through the camera part 900.

Figure 20:
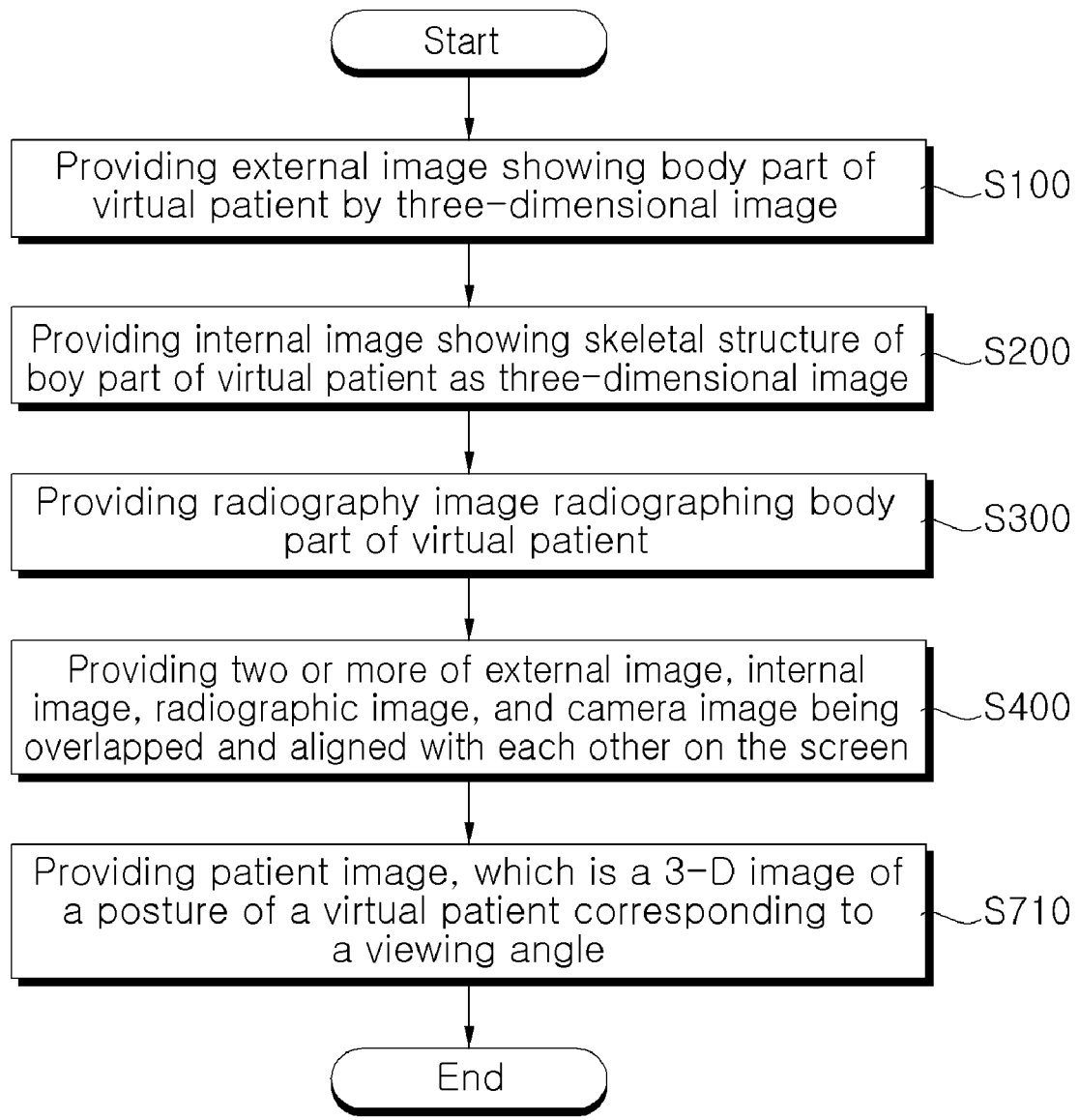
FIG. 20 is a flow chart illustrating a radiography guiding method according to another example embodiment of the present invention.
Figure 21:
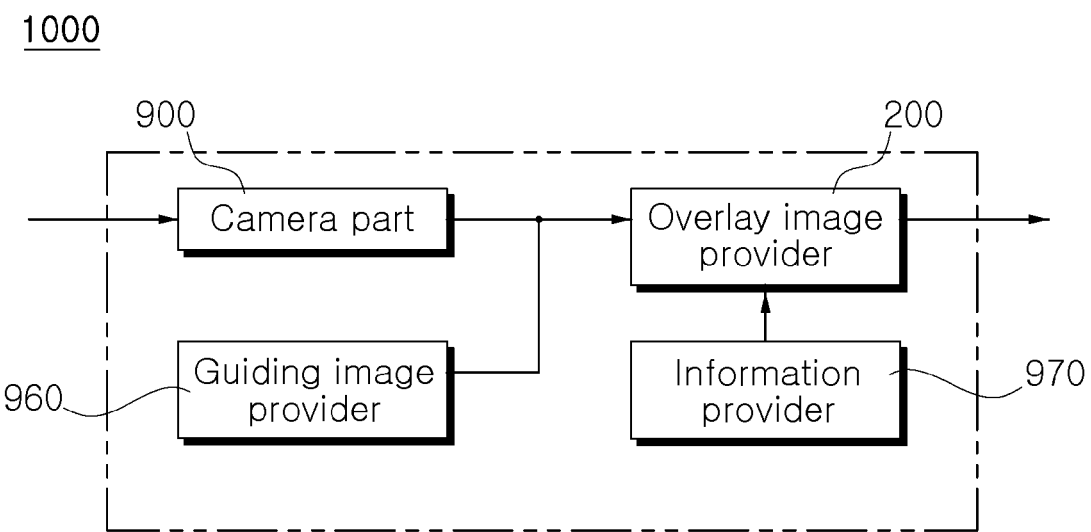
FIG. 21 is a conceptual diagram illustrating a radiography guiding method according to still another example embodiment of the present invention.
Figure 22:
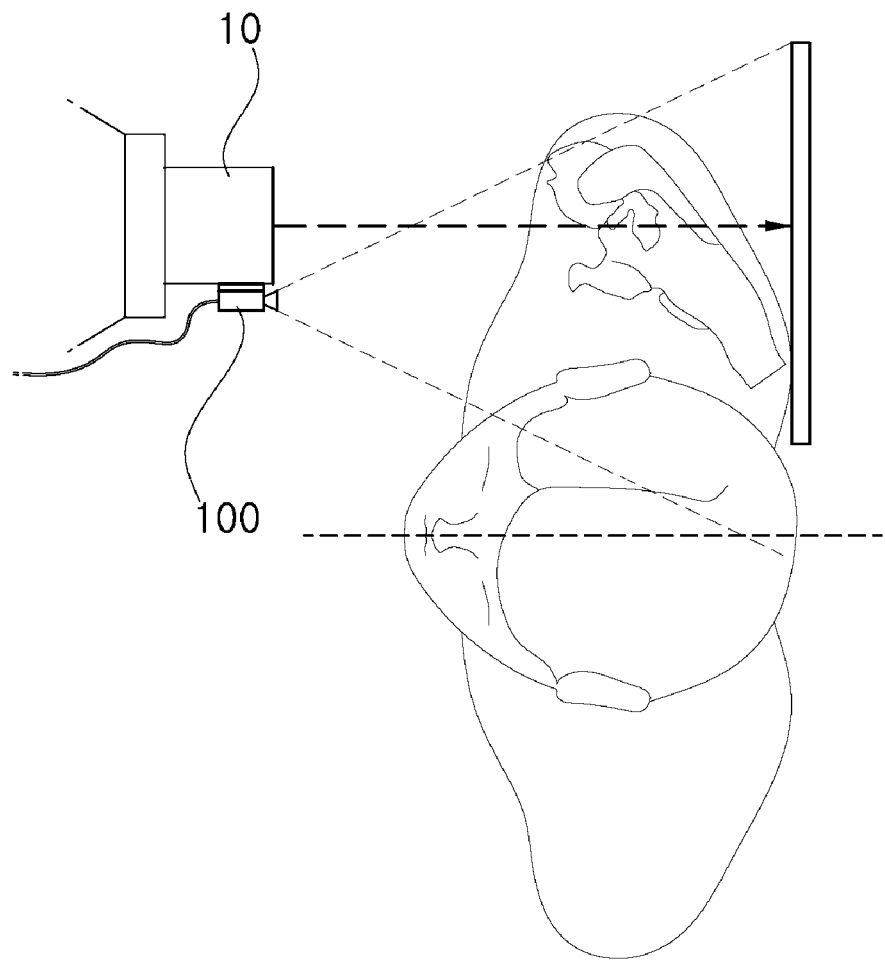
FIG. 22 is a view illustrating a camera part according to another example embodiment of the present invention.
Figure 23:
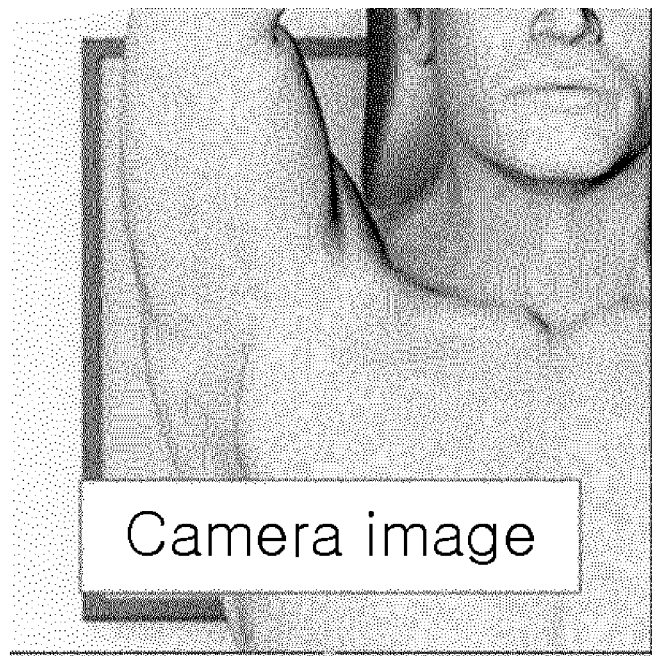
FIG. 23 is a view to explain a camera image photographed by a camera part.

FIG. 20 is a flow chart illustrating a radiography guiding method according to another example embodiment of the present invention. Since steps S100 to S400 are the same as those described above, detailed description will be omitted. In addition, step S710 shown in FIG. 20 is a step performed by the patient image provider 100, and explanation about the patient image provider 100 will be omitted here since the description of the patient image provider 100 has been described above. In addition, although not shown, in addition to the above-described patient image provider 100, at least one or more of processes performed by a medical information provider 300, an image and description provider 400, an test method provider 500, a terms provider 600, and a list provider 700) may be performed after step S400.

According to the present invention, various radiography techniques can be easily viewed and confirmed because it is easy to search for contents related to radiographic techniques, and easy to find and read detailed information about radiographic techniques. In addition, according to the present invention, a structure of the radiographic image and the accurate posture of the patient can be obtained at a glance through the overlay technique of the three-dimensional images, so that it is very easy to understand how radiographic images are taken. In addition, according to the present invention, the posture of the patient can be corrected based on the overlay image so that the patient can be taken in the correct posture.

In addition, the radiographic guiding system 1000 according to the embodiment of the present invention can be implemented in an application form and can be configured to be operated in an OS program such as iOS, Android, Windows, and the like.

Referring to FIGS. 21 to 28, the radiographic guide system 1000 according to the embodiment of the present invention includes a camera part 900, a guiding image provider 960, an overlay image provider 200, and an information provider 970.

Figure 3:
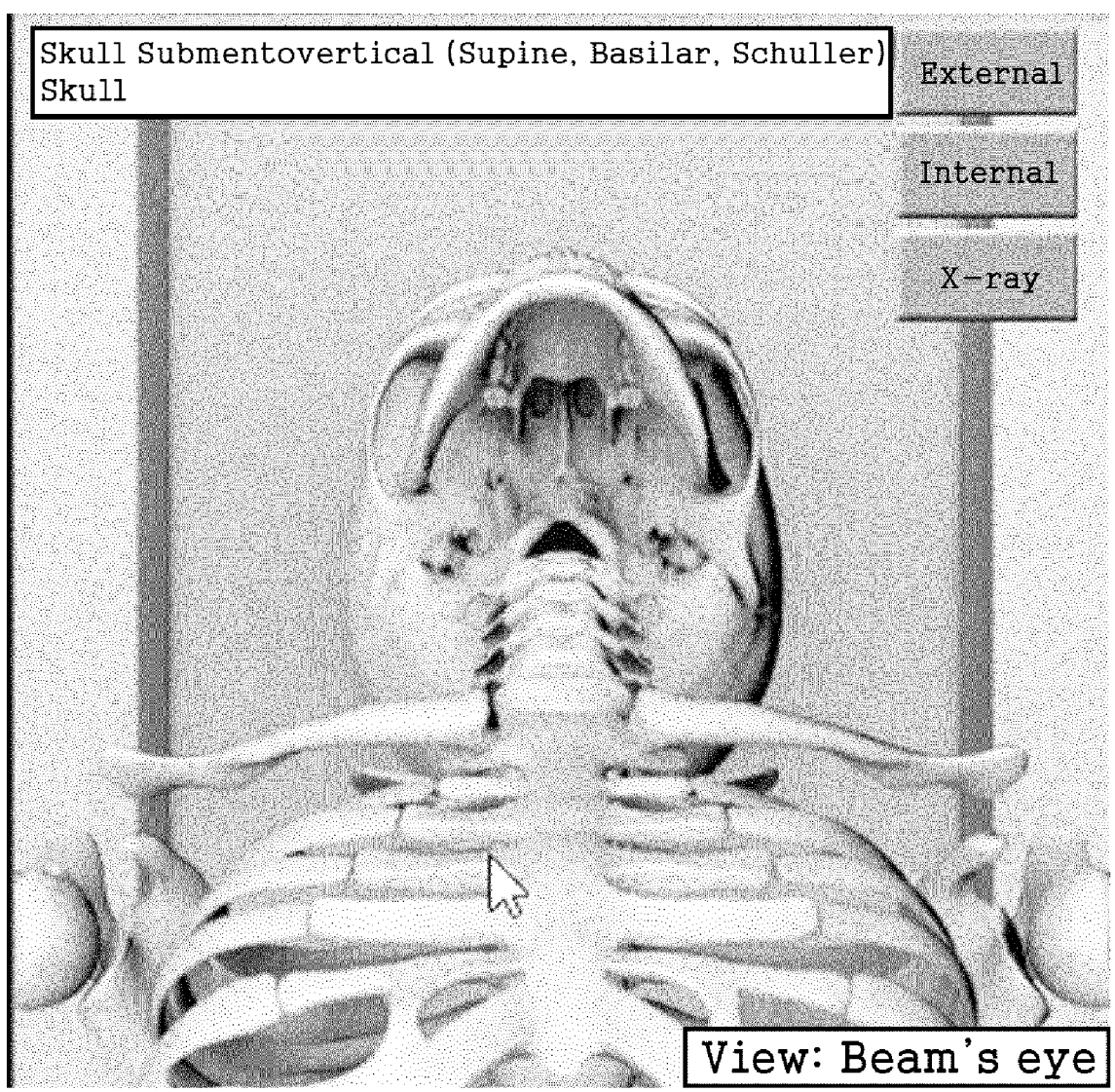
Figure 4:
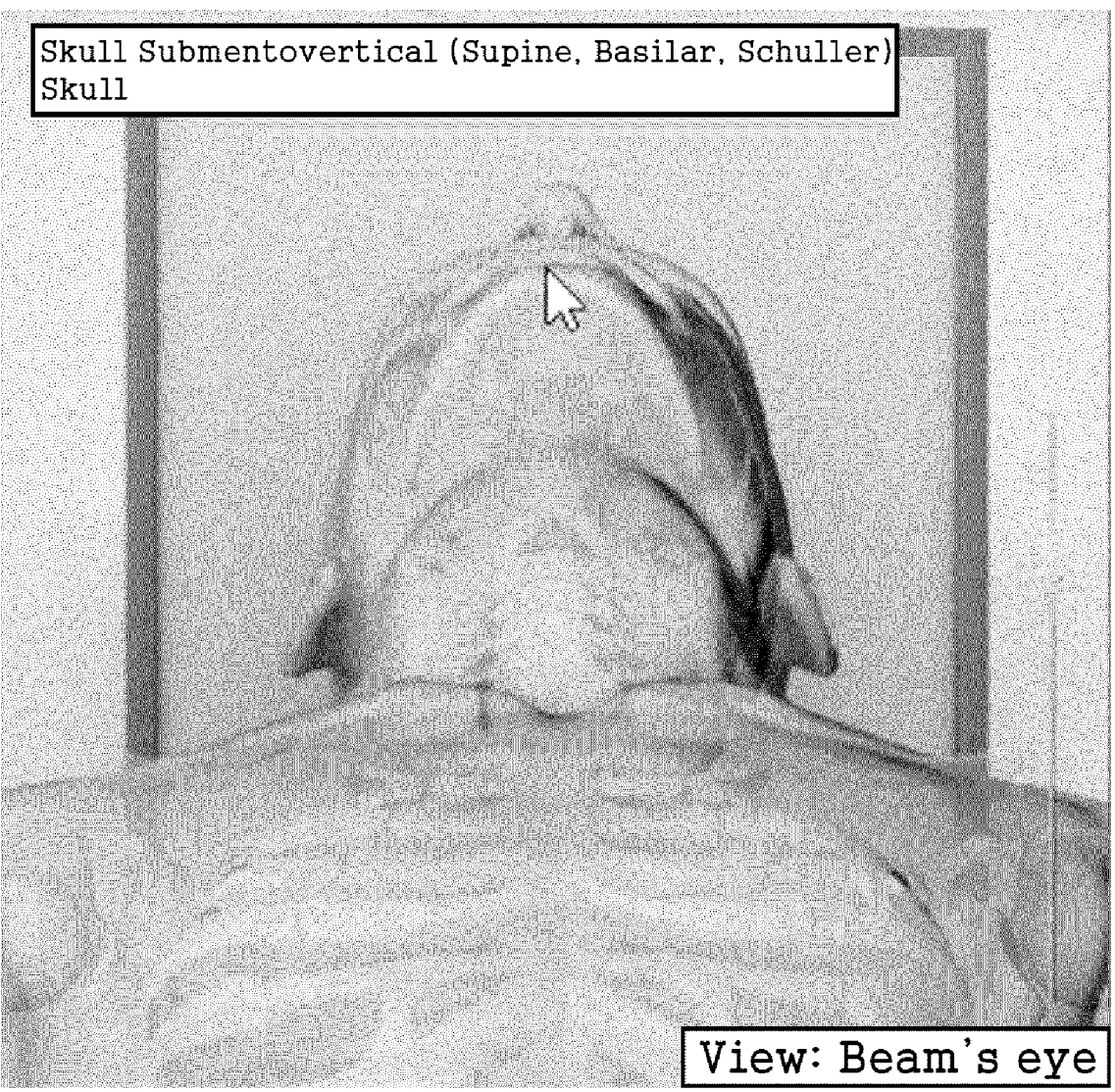

The camera part 900 may photograph a body part of a patient who is irradiated by radiation and provide a camera image which is photographed. For example, a CCD camera can be used as the camera part 900. Referring to FIG. 3, through the camera part 900, a camera image of the patient's right shoulder region can be seen.

The camera part 900 is preferably arranged so as to face a direction in which the radiation is incident. For example, referring to FIG. 22, as the camera part 900 is attached to a periphery of a X-ray tube 10 and a lens direction of the camera part 900 is adjusted so as to coincide with a direction in which a X-ray is incident, so that the camera part 900 can be arranged so as to face the direction in which the radiation is incident.

In addition, a size of the camera image taken by the camera part 900 and a size of the guiding image for guiding radiography must match with each other, and the camera image and the guiding image can be displayed on the screen with being overlapped with each other. Therefore, it is preferable that the sizes of the camera image and the guiding image are set to coincide with each other. The screen may be a screen of a touch screen, or a screen of a monitor or a display device.

The guiding image provider 960 may provide a guiding image for guiding radiography. The guiding image may be stored in a storage unit (not shown), and the guiding image may include at least one of an image of a skeletal structure representing a body of the patient and an image of an outline of the body of the patient.

Figure 24:
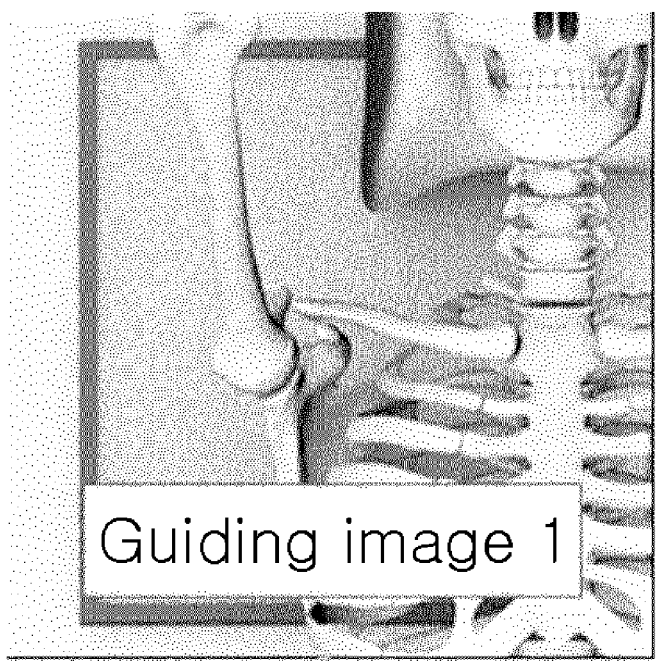
FIGS. 24 and 25 are views to explain a guide image.
Figure 25:
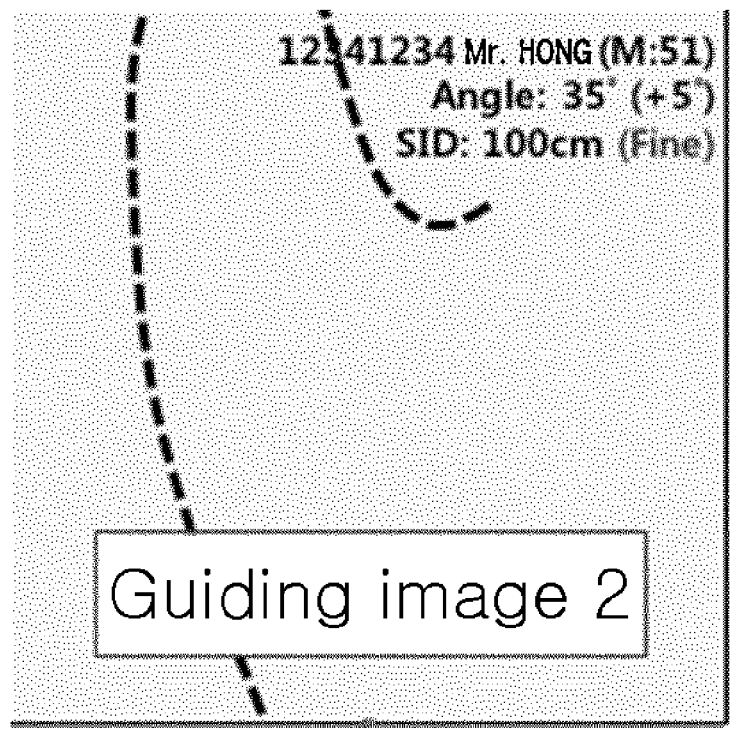

Referring to FIG. 24, an image of the skeletal structure representing the body of the patient can be seen. Referring to FIG. 25, an image representing the outline of the body of the patient can be seen. For example, the image of the skeletal structure representing the body of the patient may be represented by a three-dimensional image, and the image of the outline representing the body of the patient may be represented by a dotted line.

Figure 26:
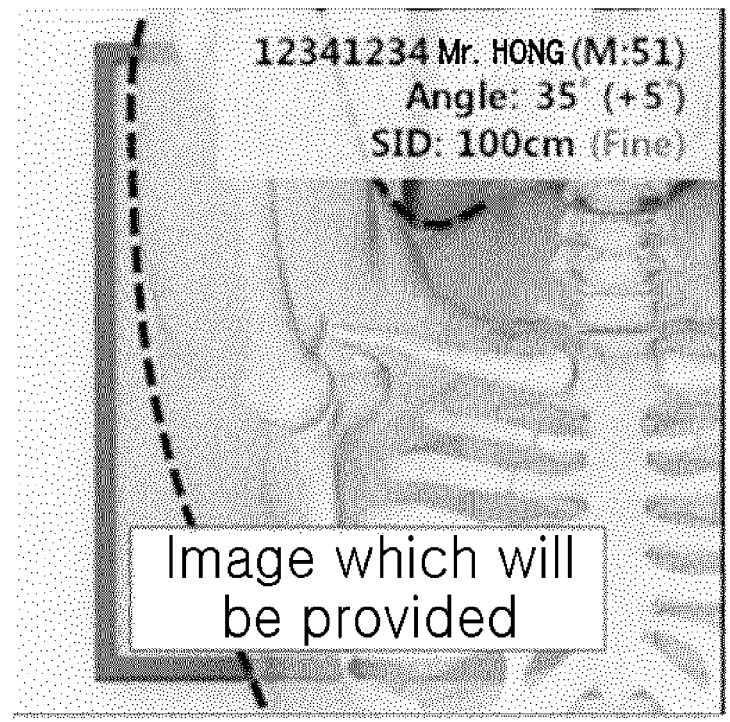
FIG. 26 is a view to explain a state in which a camera image and a guide image are displayed with being overlapped and aligned with each other.
Figure 27:
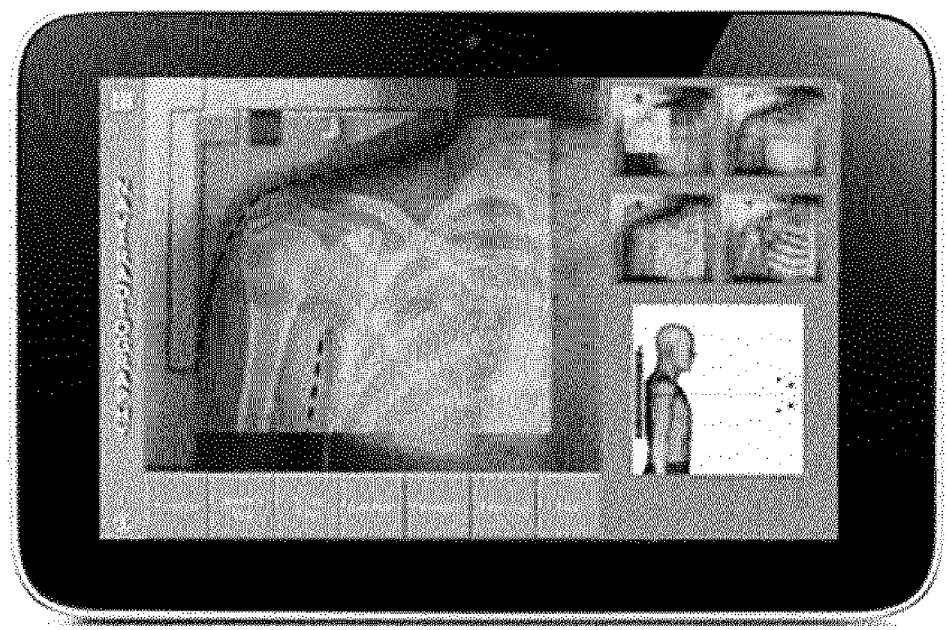
FIG. 27 is a view to explain a result displayed on a screen by a radiography guiding system according to an embodiment of the present invention.

The overlay image provider 200 may display the camera image and the guiding image being overlapped with each other on the screen. Referring to FIG. 26, it can be seen that the camera image and the guiding image are displayed on the screen with being overlapped with each other, and at least one of the camera image and the guiding image may be configured such that its transparency can be changed. Through the change of the transparency, it is very easy to check whether the camera image and the guiding image are aligned with each other.

The change of the transparency can be operated by pressing a button provided on the screen, moving a scroll bar provided on the screen, tapping the screen, or dragging the screen.

The information provider 970 may provide information necessary for correcting a posture of the patient so that the camera image and the guiding image are aligned with each other on the screen.

The information necessary for correcting the posture of the patient may include a unique number of the patient, name of the patient, gender, age, current angle of the radiation emitted from x-ray tube, reference angle of the radiation for accurate radiography, evaluation of the current angle, a current distance between a radiation detector and the patient, reference distance for accurate radiography and evaluation of the current distance, but it is not limited thereto. A variety of information that can be used to make a radiograph at a precise location on the patient can be used as the information necessary for correcting the posture of the patient.

The reference angle of the radiation for accurate radiography means the reference angle of the radiation for which the radiography can be accurately performed. The reference distance for accurate radiography means a reference distance between the x-ray tube 10 and the patient where the radiography can be accurately performed.

The evaluation of the current angle means a difference between the current angle and the reference angle. The evaluation of the current distance means a difference between current distance and the reference distance. By evaluation of the current angle and evaluation of the current distance, it is possible to easily grasp whether the current angle should be moved by a few degrees or the current distance should be moved by a few centimeters, so that the radiologist can accurately perform radiography.

Referring to FIGS. 25 and 26, the information necessary for correcting the posture of the patient can be displayed on the left or top right corner of the screen. By referring to this information, the camera image and the guiding image can be overlapped and aligned with each other.

The radiography may be performed while the camera image and the guiding image are overlapped and aligned with each other, and at least one of a radiographic image which is taken and the camera image may be stored in a storage unit. The storage unit may be, for example, an HDD, a USB, an SSD, a flash memory, or the like.

When a mixed image in which the radiographic image and the camera image are overlapped with each other is stored in the storage unit, a doctor can describe the result of radiography to the patient using the stored mixed images after radiography, and the patient can easily understand the result of the radiography and can help the patient's medical care.

When the doctor uses the mixed image to explain the result of radiography to the patient, the patient can easily understand the result because he or she can know not only his or her appearance condition but also the internal image of the body through the radiographic image. For example, in a case of radiography to a patient with a severely bent back, since the camera image representing the outline of the bent patient and the radiographic image of the bent back are simultaneously displayed, the doctor may easily explain a bone position and a bent shape or deformed state of the bone to the patient who has no expertise about the bone, so that the patient's understanding is very easy.

Figure 28:
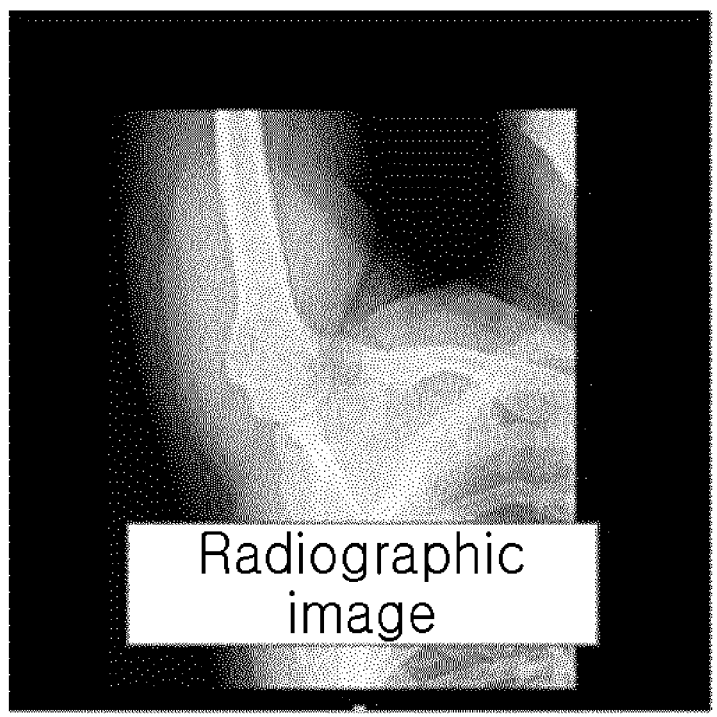
FIG. 28 is a view to explain a radiographic image.
Figure 29:
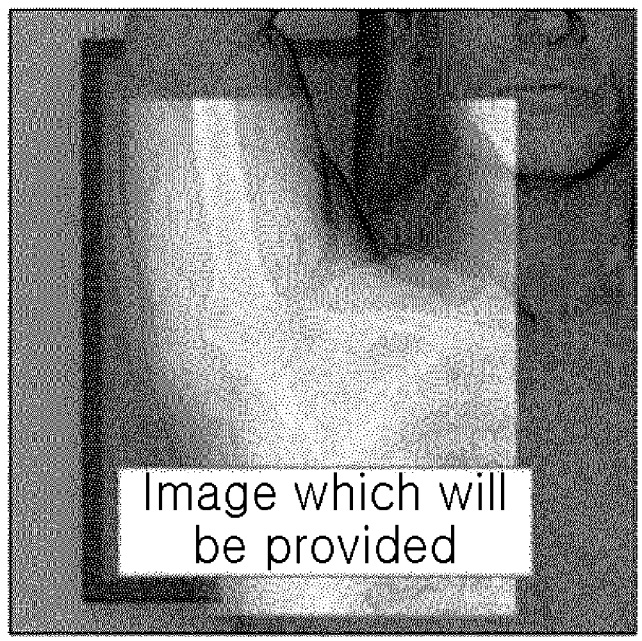
FIG. 29 is a view to explain a state in which a camera image and a radiographic image are displayed with being overlapped and aligned with each other.

In addition, the overlay image provider may display the radiographic image and the camera image with being overlapped with each other on the screen when the radiography of the body of patient is completed Referring to FIG. 28, it can be seen that the radiographic image is displayed. Referring to FIG. 29, it can be seen that the radiographic image and the camera image are displayed with being overlapped and aligned with each other.

At least one of the camera image and the radiographic image can be configured so that its transparency can be changed. For example, the change of the transparency can be operated by pressing a button provided on the screen, moving a scroll bar provided on the screen, tapping the screen, or dragging the screen.

The radiography guiding system 1000 according to the embodiment of the present invention may further include a communication unit (not shown). The camera image, the guiding image, the radiographic image, an image in which the camera image the guiding image are overlapped with each other, an image in which the camera image the radiographic image are overlapped with each other may be transferred to an external electronic device by the communication unit to display them on a display of the electronic device. Examples of electronic devices include, but are not limited to, smart phones, PDAs, mobile phones, notebooks, and computers.

The radiography guiding system 1000 according to the embodiment of the present invention can be applied in various ways such as attaching a console (radiography control computer) or a separate computer (portable computer) inside a radiography device, or embedding it into a radiography device.

In addition, the radiography guiding system 1000 according to the embodiment of the present invention may be implemented in a variety of ways, such as being embodied in a control software in a console computer.

Figure 30:
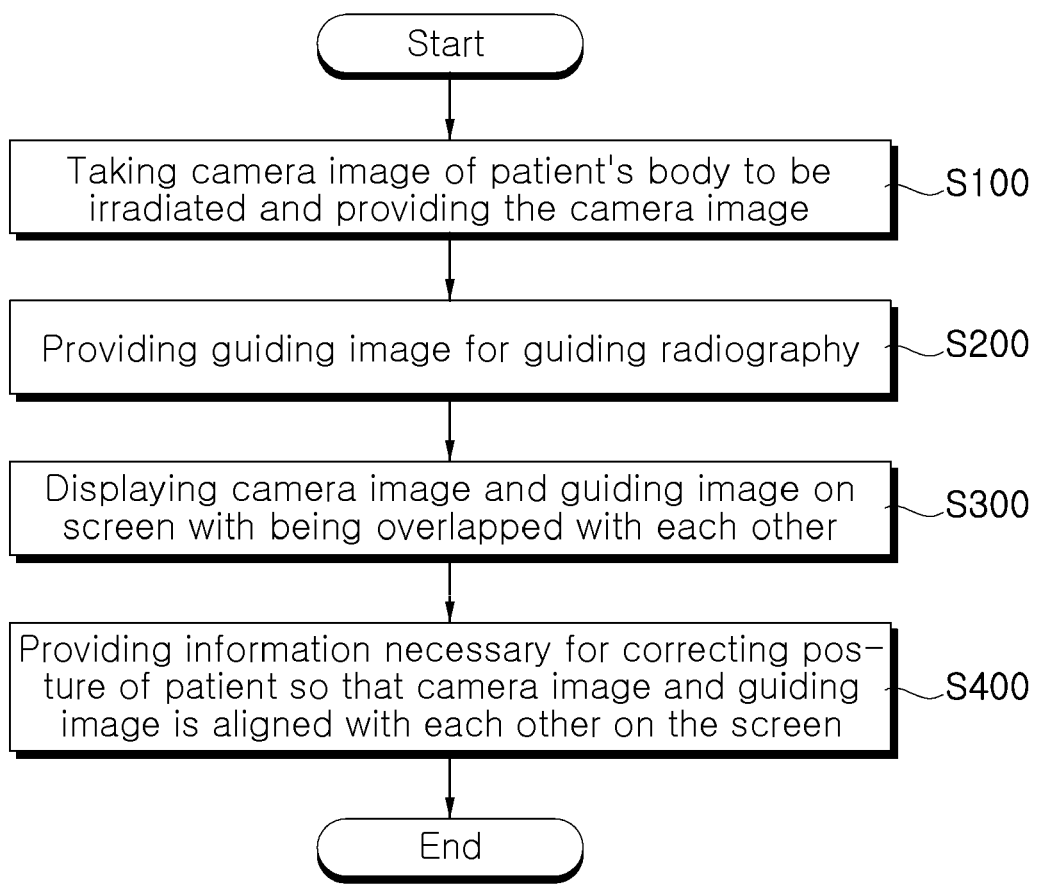
FIG. 30 is a flow chart to explain a radiography guiding method using a camera image according to an embodiment of the present invention.

Referring to FIG. 30, a radiography guiding method according to an example embodiment of the present invention may include taking a camera image of a patient's body to be irradiated and providing the camera image (S100), providing a guiding image for guiding radiography (S200), displaying the camera image and the guiding image on a screen with being overlapped with each other (S300) and providing an information necessary for correcting a posture of the patient so that the camera image and the guiding image is aligned with each other on the screen (S400).

To radiograph a patient's body, the patient's body to be irradiated by radiation is photographed, and camera image which is taken is provided. (S100). The camera image can be photographed after arranging a camera lens so as to face a direction in which the radiation is incident. The camera image can be viewed in real time through a monitor or the like.

A guiding image for guiding radiography is provided (S200).

After that, the camera image and the guiding image are displayed with being overlapped with each other on a screen (S300). By displaying the camera image and the guiding image with being overlapped with each other, it is possible to easily confirm whether the camera image and the guiding image are aligned with each other.

After that, an information necessary for correcting a posture of the patient is provided so that the camera image and the guiding image is aligned with each other on the screen (S400).

Figure 5:
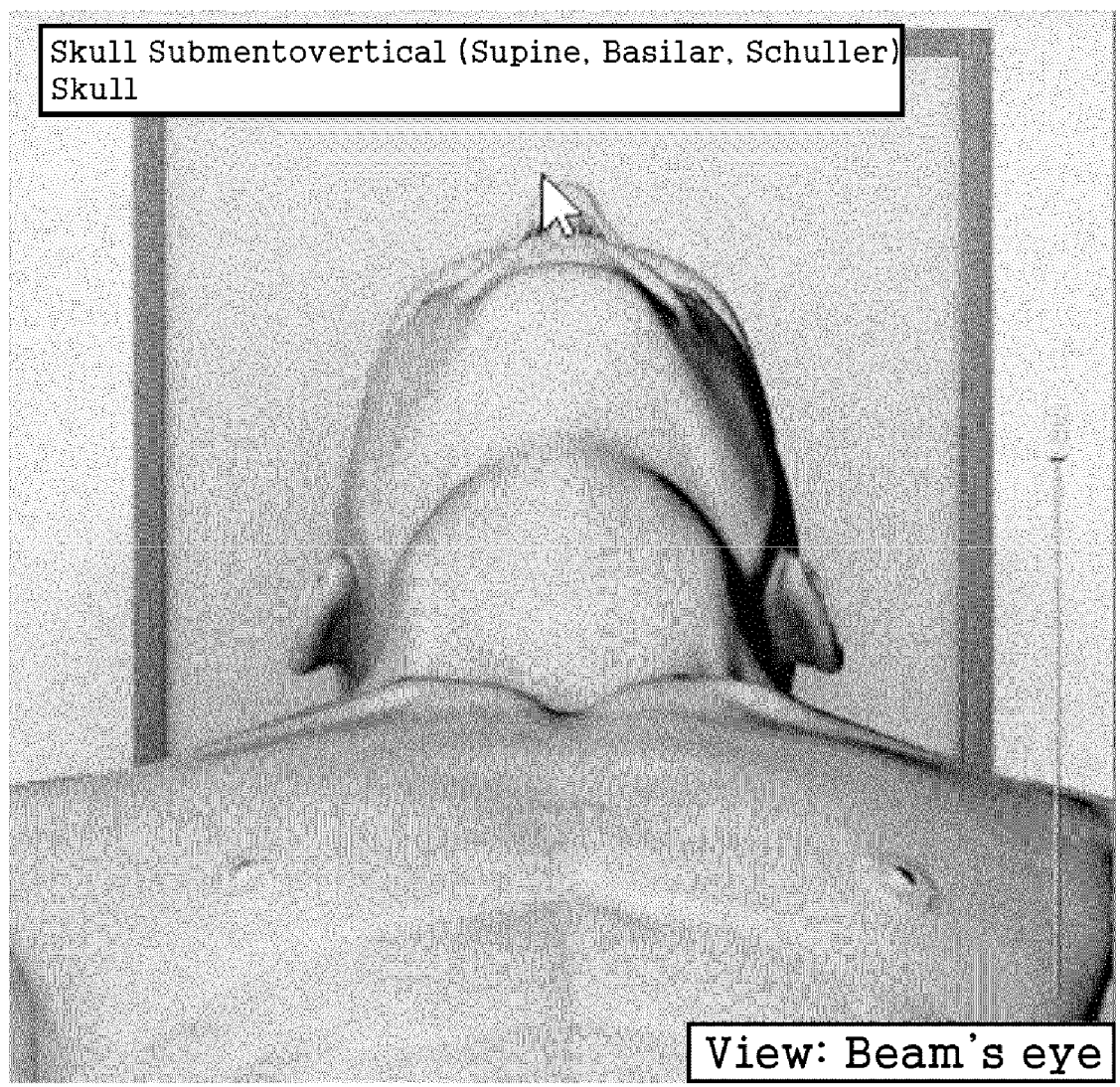
Figure 6:
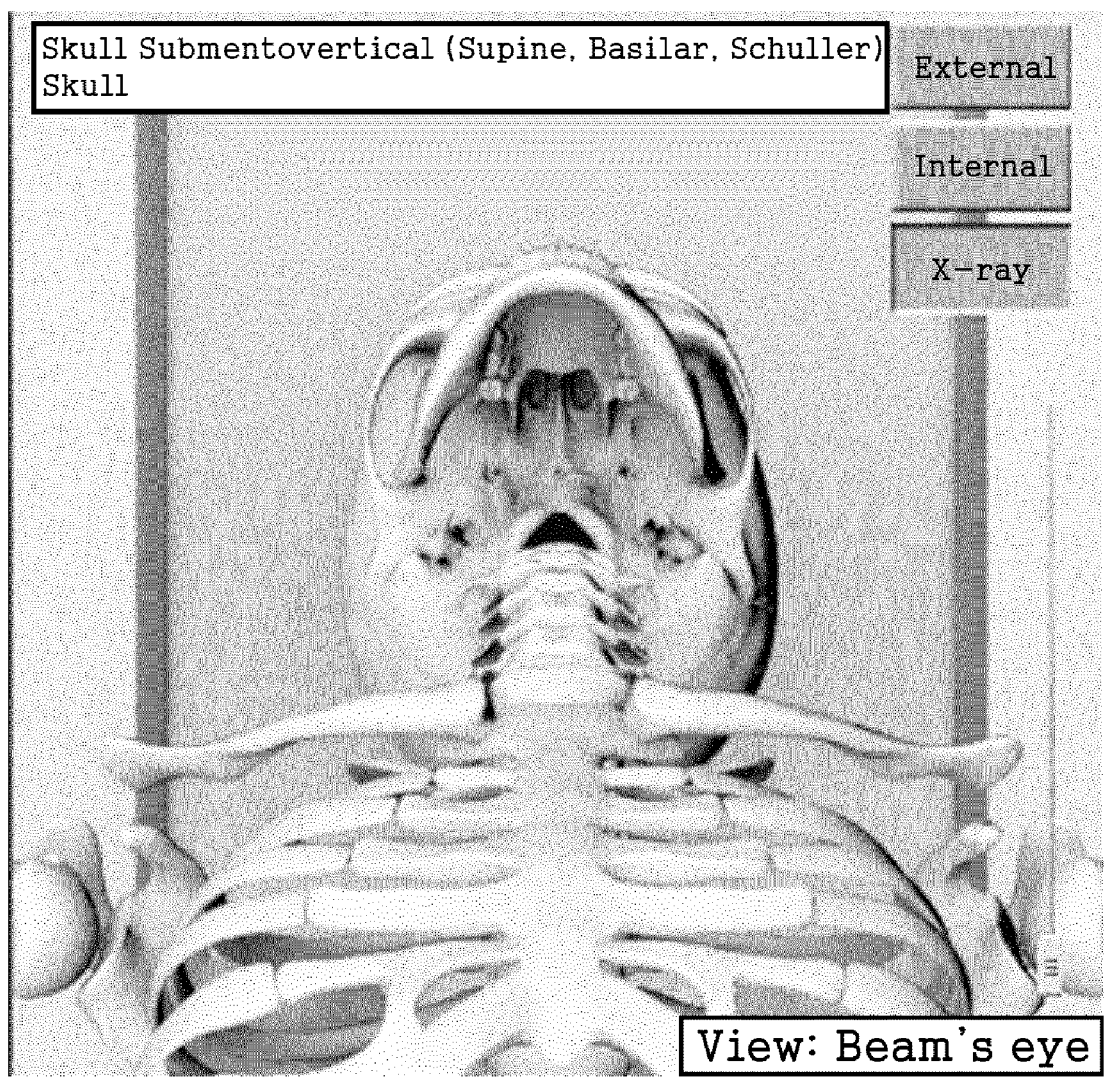
FIGS. 6 to 9 are pictures to explain a process in which transparencies of an external image and a radiographic image are changed when the external image and the radiographic image are provided to be overlapped with each other.
Figure 7:
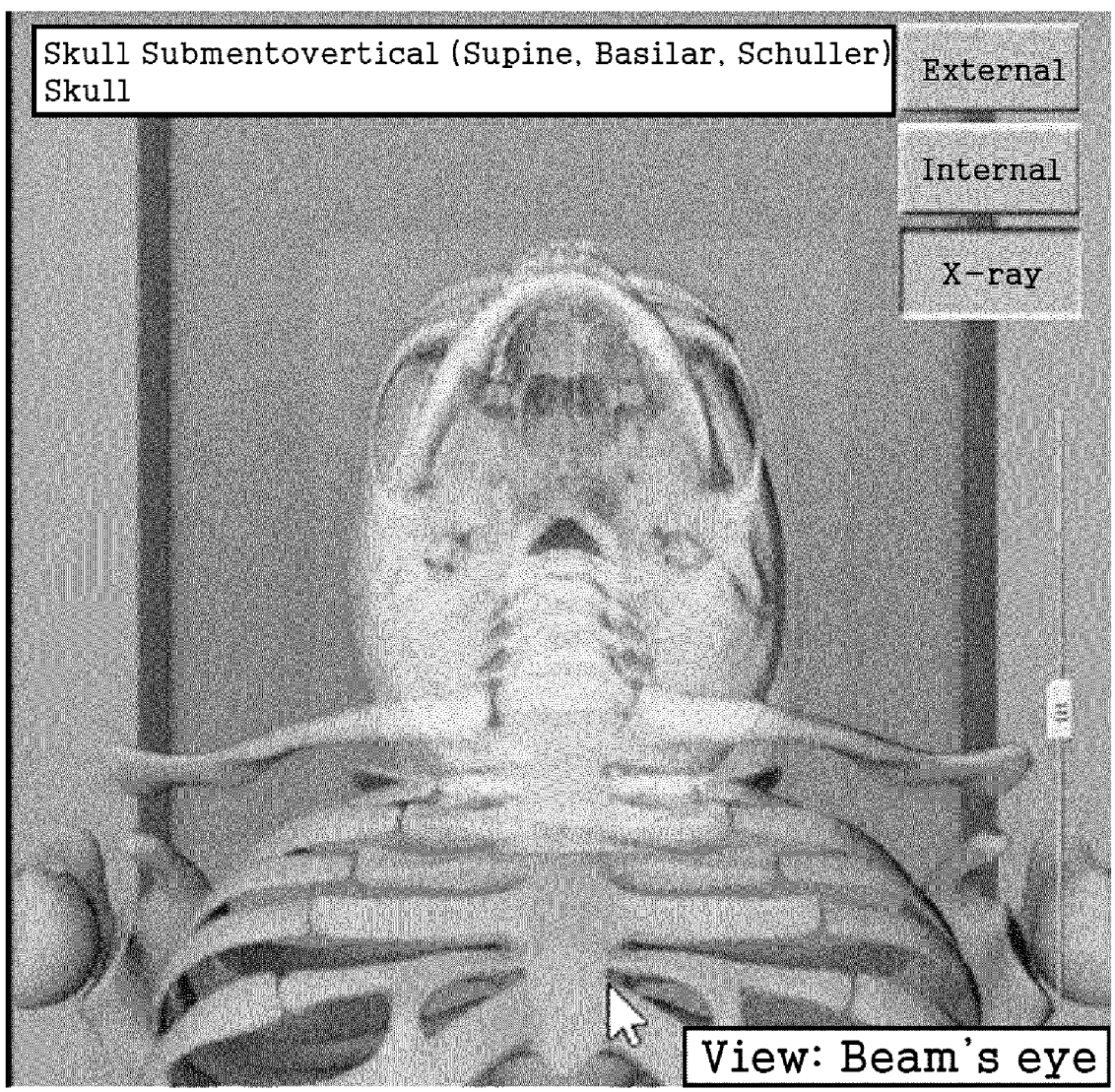
Figure 8:
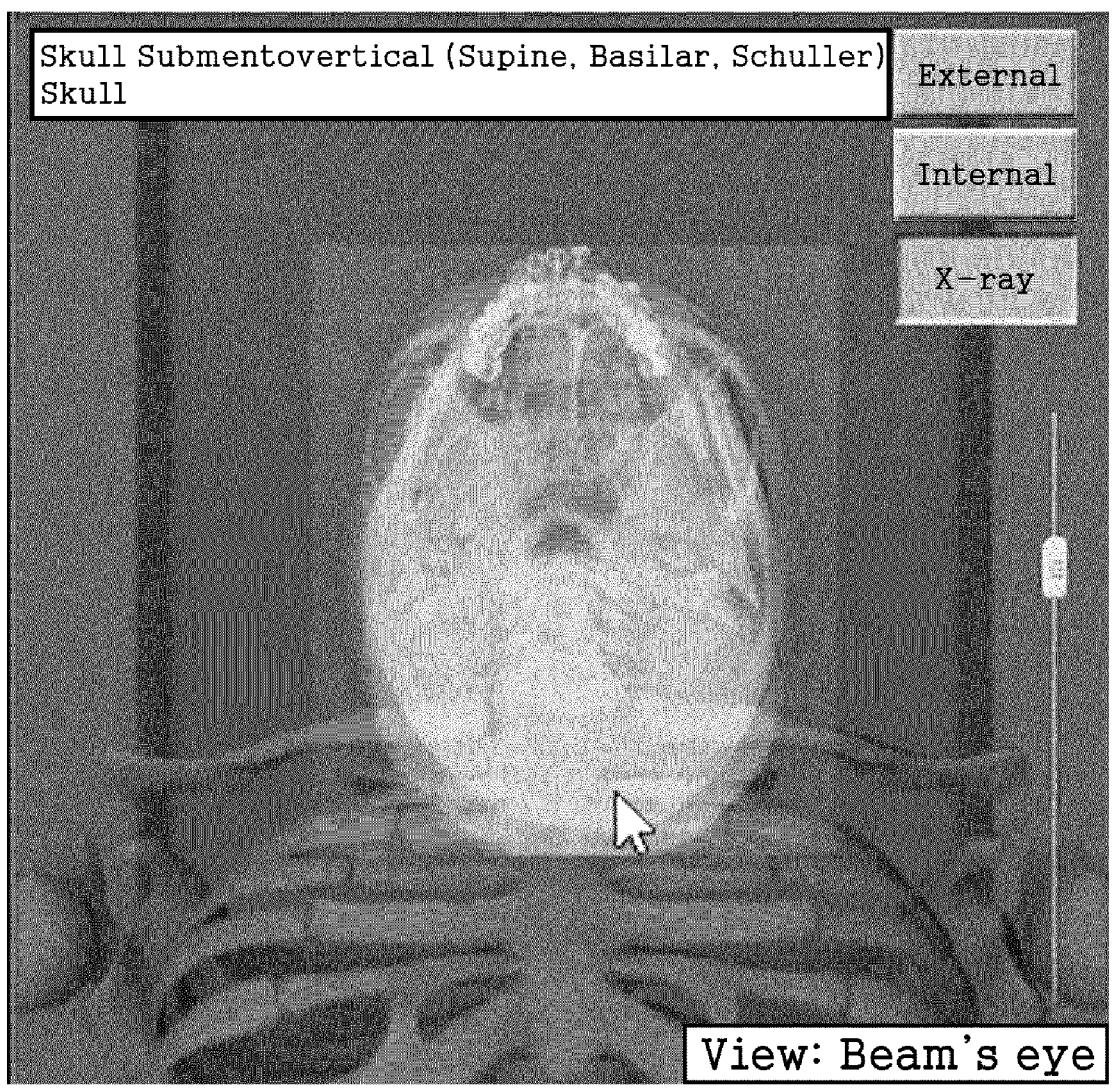
Figure 9:
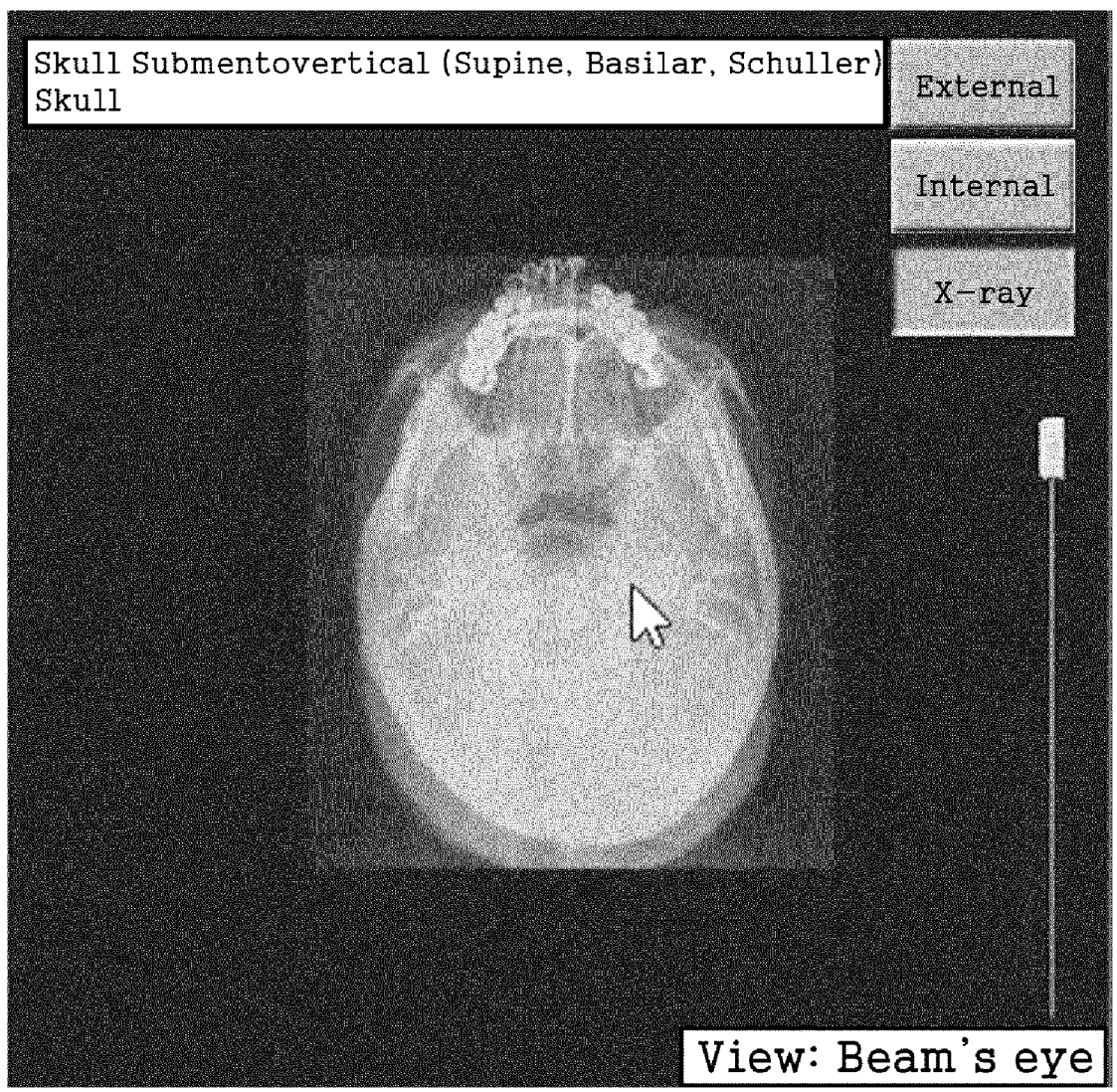

The step S300 and the step S400 can be performed at the same time. For example, as shown in FIG. 5 and FIG. 6, these may be displayed on a single screen.

Figure 31:
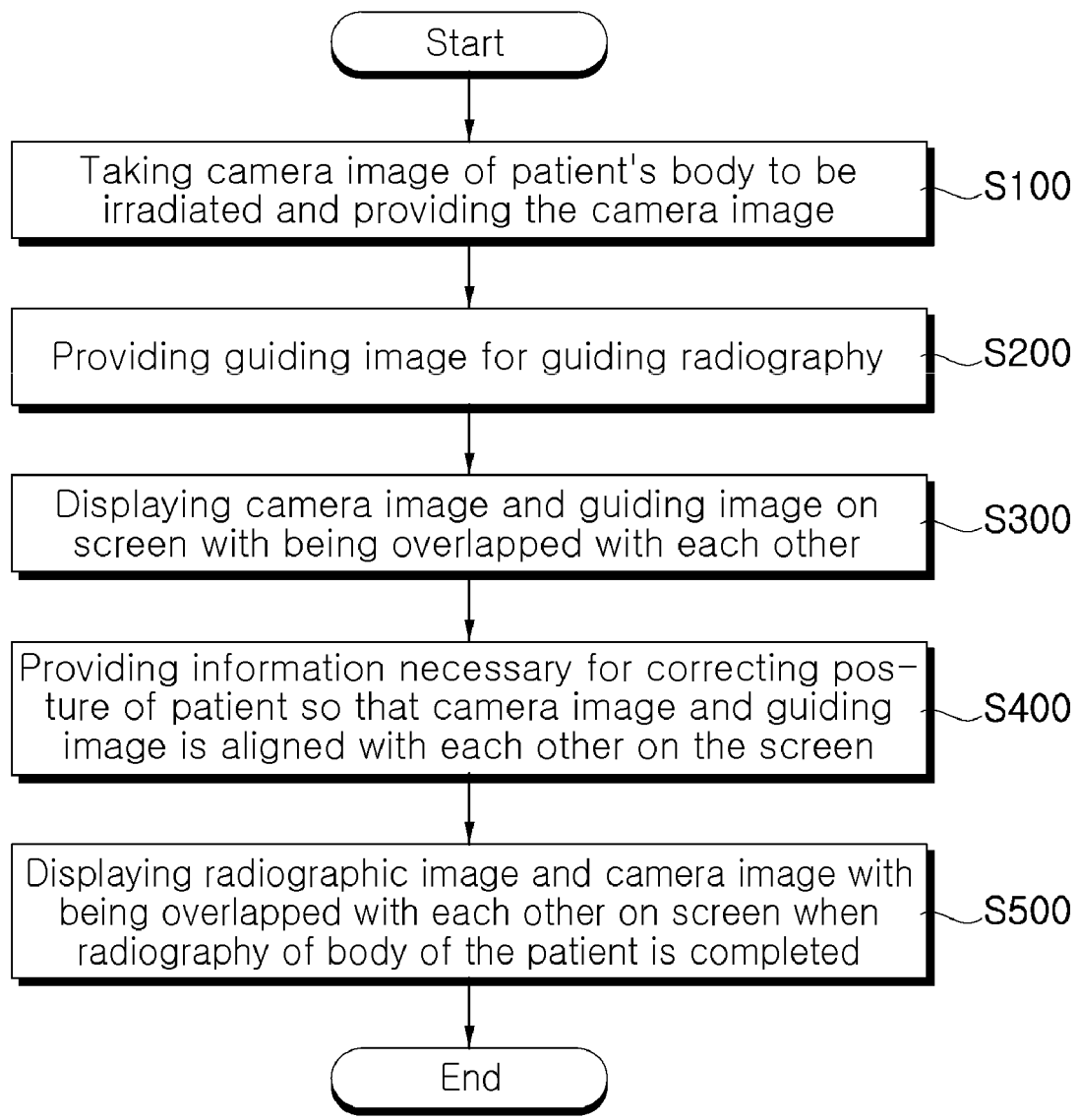
FIG. 31 is a flow chart to explain a radiography guiding method according to another embodiment of the present invention.

Referring to FIG. 31, a radiography guiding method according to another example embodiment of the present invention may include taking a camera image of a patient's body to be irradiated and providing the camera image (S100), providing a guiding image for guiding radiography (S200), displaying the camera image and the guiding image on a screen with being overlapped with each other (S300), providing an information necessary for correcting a posture of the patient so that the camera image and the guiding image is aligned with each other on the screen (S400) and displaying a radiographic image and the camera image with being overlapped with each other on the screen when the radiography of the patient's body is completed.

The steps S100 to S400 are the same as those described with reference to FIG. 30, and thus a detailed description thereof will be omitted.

Based on an information necessary for correcting a posture of a patient and whether a camera image is aligned with the guiding image, the posture of the patient can be adjusted to ensure that the radiography is accurate, and by adjusting the posture of the patient, the camera image and the guiding image can be overlapped and aligned with each other.

In this state, the body of the patient is subjected to radiography. When the radiography of the body of the patient is completed, a radiographic image and the camera image are displayed on the screen with being overlapped with each other (S500).

By confirming the radiographic image and the camera image at the same time, it is possible to confirm whether the radiographic image is accurately taken.

Referring to FIG. 32, a radiography guiding method according to another embodiment of the present invention may include taking a camera image of a body of patient to be irradiated and providing the camera image (S100), providing a guiding image for guiding radiography (S200), displaying the camera image and the guiding image on a screen with being overlapped with each other (S300), providing an information necessary for correcting a posture of the patient so that the camera image and the guiding image is aligned with each other on the screen (S400), displaying a radiographic image and the camera image with being overlapped with each other on the screen when the radiography of the body of the patient is completed (S500) and storing a mixed image in which the radiographic image and the camera image are overlapped on the screen. (S600)

The steps S100 to S500 are the same as those described with reference to FIG. 31, and thus a detailed description thereof will be omitted.

After the step S500, a mixed image in which the radiographic image and the camera image are overlapped on the screen is stored.

The stored mixed images are medical information that a doctor can use to describe the radiographic results to the patient, and as described above, the patient can easily understand the results of his or her radiography and can be helpful to the patient's care.

According to the radiography guiding system and method according to the present invention, since the structure of the radiographic image and the accurate posture of the patient can be obtained at a glance through the overlay technique of the three-dimensional images, learner's understanding of radiography is greatly improved.

In addition, according to the radiography guiding system and method according to the present invention, the learner learning the radiography can understand the radiography in an easy-to-understand way through the three-dimensional image.

In addition, according to the radiography guiding system and method according to the present invention, it is possible to replace a thick book for learning the radiography and to easily search the contents of the radiography.

In addition, according to the radiography guiding system and method according to the present invention, the patient can be taken radiograph in correct posture.

The invention claimed is:

1. A radiography guiding system, comprising:
a patient image provider to provide a patient image, which is a three dimensional (3-D) image of a posture of a virtual patient corresponding to a viewing angle with an information of one of location information, on which the virtual patient is to be located, a radiographic direction and angle of radiography, on a screen; and
an overlay image provider to generate an external image which is a 3-D image of an external appearance of a body of the virtual patient corresponding to the location information, the radiographic direction and the angle of radiography, an internal image which is 3-D image of a skeletal structure of the body, and a radiographic image of the body,
wherein the overlay image provider provides an overlay image, in which the internal image, the external image, and the radiographic image are overlapped and aligned with each other, to the screen.

2. The radiography guiding system of claim 1, wherein at least one of the external image, the internal image, and the radiographic image is configured to change its transparency.

3. The radiography guiding system of claim 2, wherein the transparency is changed when a button provided on the screen is pressed, a scroll bar is moved, the screen is tapped, or the screen is dragged.

4. The radiography guiding system of claim 1, further comprising a medical information provider which is configured to enlarge the radiographic image, and provides medical information on a main anatomical location of the radiographic image.

5. The radiography guiding system of claim 1, further comprising an image and description provider which provides a description of the overlay image.

6. The radiography guiding system of claim 5, wherein the description comprises at least one or more of a classification of radiography, a title of radiography, a target location of radiography, a size of a cassette, a photographing distance, a photographing center point, a breathing state of the patient, a posture adjustment of the patient, a radiation field, an evaluation of the radiographic image, a tube voltage, a tube current and a radiographic tip.

7. The radiography guiding system of claim 1, further comprising a test method provider which provides a test method associated with radiography and important test parameters related to the test method.

8. The radiography guiding system of claim 1, further comprising a terms provider which provides an image of the skeletal structure of the body and anatomical names constituting the skeletal structure.

9. The radiography guiding system of claim 1, further comprising a list provider which provides a list of radiographic techniques for each of the anatomical names.

10. The radiography guiding system of claim 1, further comprising a search provider which provides search function about radiography techniques.

11. The radiography guiding system of claim 1, further comprising:
a camera part which photographs a body part of the patient; and
a real-time overlay image provider which overlays the overlay image provided by the overlay image provider and a camera image provided by the camera part on the screen.

12. A radiography guiding system, comprising:
a camera part which photographs a body of a patient, who is irradiated by radiation, and provides a camera image which is photographed;
a guiding image provider which provides a guiding image for guiding radiography;
an overlay image provider which displays the camera image and the guiding image being overlapped with each other on a screen; and
an information provider which provides information necessary for correcting a posture of the patient so that the camera image and the guiding image are aligned with each other on the screen.

13. The radiography guiding system of claim 12, wherein the camera part is arranged to face a direction in which the radiation is incident.

14. The radiography guiding system of claim 12, wherein the guide image comprises at least one of an image of a skeletal structure representing the body of the patient and an image of an outline of the body of the patient.

15. The radiography guiding system of claim 12, wherein the overlay image provider displays a radiographic image and the camera image with being overlapped with each other on the screen when the radiography of the body of patient is completed.

16. The radiography guiding system of claim 15, wherein at least one of the camera image, the guiding image, and the radiographic image is configured to change its transparency.

17. The radiography guiding system of claim 16, wherein the transparency is changed when a button provided on the screen is pressed, a scroll bar is moved, the screen is tapped, or the screen is dragged.

18. The radiography guiding system of claim 12, wherein the information necessary for correcting the posture of the patient comprises at least one or more of a unique number of the patient, name of the patient, gender, age, current angle of the radiation emitted from x-ray tube, reference angle of the radiation for accurate radiography, evaluation of the current angle, a current distance between a radiation detector and the patient, reference distance for accurate radiography and evaluation of the current distance.

19. A radiography guiding method, comprising:
taking a camera image of a body of patient to be irradiated and providing the camera image;
providing a guiding image for guiding radiography;
displaying the camera image and the guiding image on a screen with being overlapped with each other; and
providing an information necessary for correcting a posture of the patient so that the camera image and the guiding image are aligned with each other on the screen.

20. The radiography guiding system of claim 19, further comprising:
displaying a radiographic image and the camera image with being overlapped with each other on the screen when the radiography of the body of the patient is completed.

* * * * *